US008648599B2

(12) United States Patent
Kimura

(10) Patent No.: US 8,648,599 B2
(45) Date of Patent: Feb. 11, 2014

(54) MAGNETIC RESONANCE IMAGING APPARATUS AND MAGNETIC RESONANCE IMAGING METHOD

(75) Inventor: Tokunori Kimura, Yaita (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 327 days.

(21) Appl. No.: 13/228,698

(22) Filed: Sep. 9, 2011

(65) Prior Publication Data

US 2012/0074940 A1    Mar. 29, 2012

(30) Foreign Application Priority Data

Sep. 28, 2010    (JP) ................................ 2010-217981

(51) Int. Cl.
*G01V 3/00*    (2006.01)

(52) U.S. Cl.
USPC ........................................ 324/318; 324/309

(58) Field of Classification Search
USPC ............................ 324/300–322; 600/407–445
See application file for complete search history.

(56) References Cited

U.S. PATENT DOCUMENTS

2008/0081987 A1*   4/2008   Miyazaki ...................... 600/410
2011/0098552 A1    4/2011   Takai

FOREIGN PATENT DOCUMENTS

JP            7-23929       1/1995
JP        2010-172383    8/2010

OTHER PUBLICATIONS

G. McGibney et al., "Quantitative Evaluation of Several partial Fourier Reconstruction Algorithms used in MRI", Magnetic Resonance in Medicine, vol. 30, Issue 1, pp. 51-59, Jul. 1993.

* cited by examiner

*Primary Examiner* — Brij Shrivastav
(74) *Attorney, Agent, or Firm* — Nixon & Vanderhye PC

(57) ABSTRACT

According to one embodiment, a magnetic resonance imaging apparatus includes an imaging unit and data processing condition setting unit. The imaging unit is configured to acquire magnetic resonance data corresponding to a sampling region asymmetric in a wave number direction in k-space from an object to generate image data based on the magnetic resonance data by data processing including phase correction and filter processing for obtaining a complex conjugate. The data processing condition setting unit is configured to set a condition for the data processing according to an imaging condition influencing a phase distribution used for the phase correction or the phase distribution.

19 Claims, 23 Drawing Sheets

(A) PRE-SCAN (B) IMAGE SELECTION (C) IMAGING SCAN

MAGNETIC RESONANCE IMAGING APPARATUS AND MAGNETIC RESONANCE IMAGING METHOD

CROSS REFERENCES TO RELATED APPLICATIONS

This application is based upon and claims the benefit of priority from Japanese Patent Application No. 2010-217981, filed Sep. 28, 2010; the entire contents of which are incorporated herein by reference.

FIELD

Embodiments described herein relate generally to a magnetic resonance imaging apparatus and a magnetic resonance imaging method.

BACKGROUND

MRI is an imaging method which excites nuclear spin of an object set in a static magnetic field with a RF (radio frequency) signal having the Larmor frequency magnetically and reconstruct an image based on NMR (nuclear magnetic resonance) signals generated due to the excitation.

AFI is known as an imaging method for MRI. In the AFI method, asymmetric data is sampled in the wave number direction in k-space and a phase distribution estimated based on the sampled self data is used to phase correction, and subsequently image data is reconstructed. By the AFI method, image data equivalent to one generated from data symmetrically sampled in k-space can be generated.

For the AFI method, various methods such as Margosian method, FIR (finite impulse response) method, MoFIR (Modified FIR) method, POCS (projection on to convex sets) method, hybrid method and the like are suggested. Further, another asymmetric data sampling method, by which data is asymmetrically sampled in k-space and FT (Fourier transform) is performed after 0-filling on parts having no data, is known though the method is not an AFI method.

In the Margosian method, a homodyne filter as a window function is applied to asymmetrically sampled k-space data, and subsequently, r-space data corresponding to the asymmetric k-space data is generated by FT. On the other hand, a phase distribution is estimated based on symmetrically sampled k-space data in a low frequency region near the center in k-space out of the asymmetrically sampled k-space data. Then, a phase correction using the estimated phase distribution is performed on the r-space data corresponding to the asymmetric k-space data.

The POCS method is an improved Margosian method in which POCS loop processing is performed after the Margosian method. The POCS loop processing is a processing to converge a change in imaginary part not to exceed a threshold by repeating realization processing, compound processing and phase correction processing. The realization processing is processing for making the imaginary part of the r-space data after the phase correction zero to remain the real part. The compound processing is processing for combining a non-sampling part of k-space data, which is obtained by returning a phase of the realized r-space data and subsequently IFT (inverse Fourier transform), with a sampling part of the original data. The phase correction processing is applied to r-space data obtained by FT of the k-space data after the compound processing. The POCS method is based on the principle that the imaginary part of the r-space data becomes zero so long as the phase correction is complete. The POCS method can reduced errors in the phase correction occurring due to the homodyne filter processing in the Margosian method by repeating the POCS loop processing a few times.

On the other hand, in the FIR method, the phase correction is performed before applying the homodyne filter to the asymmetrically sampled k-space data. Specifically, in the FIR method, the phase correction is performed to the r-space data generated by FT of the asymmetric k-space data, and subsequently, the r-space data after the phase correction is transformed to k-space data by IFT. Then, the homodyne filter is applied to the k-space data after the phase correction. In this FIR method, the phase correction is performed before the homodyne filter processing though the data processing period becomes longer than that in the Margosian method by two times FT. Therefore, errors in the phase correction due to the homodyne filter processing can be reduced.

The MoFIR method is an improved FIR method in which the phase distribution for the phase correction is estimated based on whole k-space data including the part where the k-space data is asymmetrically sampled as well as the low frequency region where the k-space data is symmetrically sampled. Specifically, the MoFIR method estimates the phase distribution for the phase correction based on the whole k-space data asymmetrically sampled while the FIR method estimates the phase distribution in a low frequency region near the center of k-space for the phase correction from the k-space data only in the low frequency region. Therefore, the MoFIR method makes it possible to estimate a phase distribution in a higher frequency region compared to the FIR method though the estimated phase distribution differs from the actual phase distribution. Consequently, the MoFIR method yields reduction of phase correction errors due to the homodyne filter processing in the Margosian method and the FIR method.

On the other hand, 0-filling, which is the simplest reconstruction method based on asymmetrically sampled data, generates blurring in images. However, in case of asymmetrically sampling at a relatively low asymmetric degree, such as a case data more than 70% is symmetrically sampled, blurring in images becomes acceptable. In addition, 0-filling does not require special processing and does not generate artifacts due to excessive phase correction in the AFI. Therefore, 0-filling is still used abundantly when an asymmetric degree is relatively low.

The hybrid method is a method derived by combining 0-filling with the AFI method. That is, the hybrid method is a technique in which a 0-fill image generated by 0-filling is combined with an AFI image generated by the AFI by a weighted addition. More specifically, the weight is adjusted so that parts each having a larger difference in phase or amplitude between the 0-fill image and the AFI image become the 0-fill image more while parts each having a smaller difference become the AFI image more.

The conventional AFI has a problem that artifacts sometimes occur more remarkably than 0-filling when a phase error becomes large due to failure in estimation of the phase. Accordingly, it is desired to generate image data from data asymmetrically sampled in k-space with accuracy equivalent to that of an image generated from symmetrically sampled data while increase of a data processing period necessary for image reconstruction is minimized.

The object of the present invention is to provide a magnetic resonance imaging apparatus and a magnetic resonance imaging method which can generate image data having higher accuracy based on MR data asymmetrically sampled in k-space with suppressing increase of a data processing period.

DETAILED DESCRIPTION

In general, according to one embodiment a magnetic resonance imaging apparatus includes an imaging unit and data processing condition setting unit. The imaging unit is configured to acquire magnetic resonance data corresponding to a sampling region asymmetric in a wave number direction in k-space from an object to generate image data based on the magnetic resonance data by data processing including phase correction and filter processing for obtaining a complex conjugate. The data processing condition setting unit is configured to set a condition for the data processing according to an imaging condition influencing a phase distribution used for the phase correction or the phase distribution.

In addition, a magnetic resonance imaging method according to an embodiment of the present invention includes acquiring magnetic resonance data corresponding to a sampling region asymmetric in a wave number direction in k-space from an object to generate image data based on the magnetic resonance data by data processing including phase correction and filter processing for obtaining a complex conjugate; and setting a condition for the data processing according to an imaging condition influencing a phase distribution used for the phase correction or the phase distribution.

A magnetic resonance imaging apparatus and a magnetic resonance imaging method according to embodiments of the present invention will be described with reference to the accompanying drawings.

Figure 1:
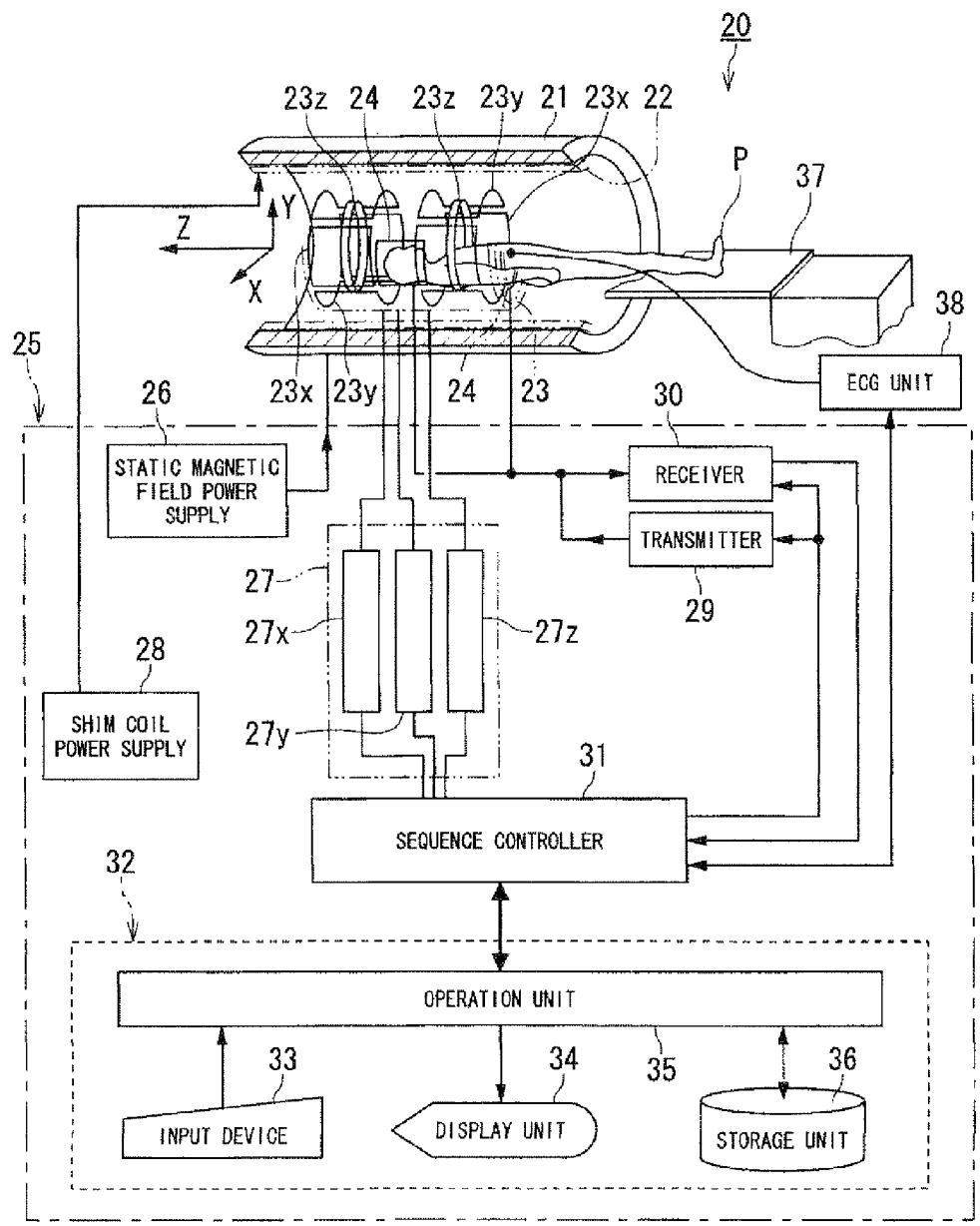
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with at least one of the transmitter 29 and the receiver 30. The transmission RF coil 24 has a function to transmit a RF signal given from the transmitter 29 to the object P. The reception RF coil 24 has a function to receive a MR signal generated due to an nuclear spin inside the object P which is excited by the RF signal to give to the receiver 30.

Figure 2:
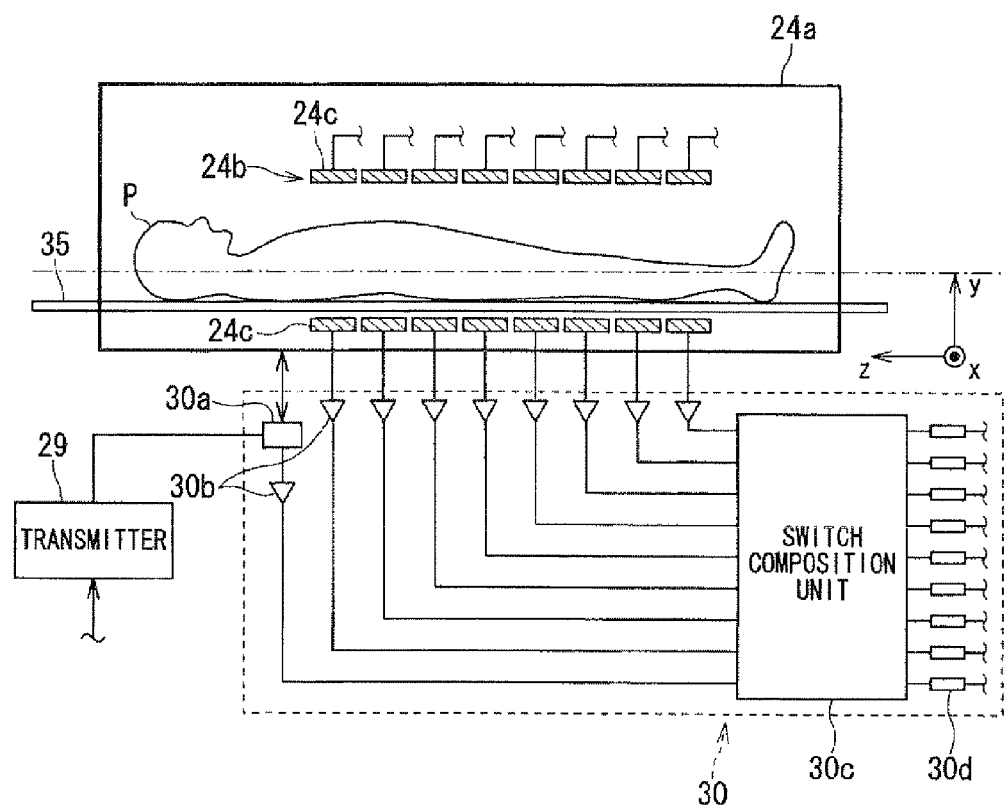
FIG. 2 is a diagram showing an example of detail construction of the RF coil shown in FIG. 1.

FIG. 2 is a diagram showing an example of detail structures of the RF coils 24 shown in FIG. 1.

As shown in FIG. 2, the RF coils 24 include a cylindrical WB (whole-body) coil 24a, and a phased array coil 24b. The phased array coil 24b includes a plurality of coil elements 24c, and a plurality of the coil elements 24c are arranged on each of the body surface side and the back surface side of the object P.

On the other hand, the receiver 30 includes a duplexer 30a, amplifiers 30b, a switch composition unit 30c, and reception circuits 30d. The duplexer 30a is connected to the transmitter 29, the WB coil 24a, and the amplifier 30b for the WB coil 24a. The amplifiers 30b are provided by the total number of the coil elements 24c and the WB coil 24a, and each connected to a respective one of the coil elements 24c and the WB coil 24a. The switch composition unit 30c consists of a single piece or a plurality of pieces. The input side of the switch composition unit 30c is connected to the plurality of surface coil units 24c or the WB coil 24a through the plurality of amplifiers 30b. The reception circuits 30d are provided by a desired number such as to be smaller than or equal to the total number of the coil elements 24c and the WB coil 24a, and disposed on the output side of the switch composition unit 30c.

The WB coil 24a can be used as a coil for the transmission of RF signals. As a coil for the reception of NMR signals, each of the coil elements 24c can be used. Furthermore, the WB coil 24a can also be used for a receiving coil.

Therefore, the duplexer 30a is configured so as to provide the WB coil 24a with RF signals for transmission, outputted from the transmitter 29, while providing the switch composition unit 30c with NMR signals received in the WB coil 24a via the amplifiers 30b in the receiver 30. An NMR signal received in each of the coil elements 24c is outputted to the switch composition unit 30c via a respective one of the amplifiers 30b.

The switch composition unit 30c is configured so as to perform composition processing and switching with respect to NMR signals received from the coil elements 24c or the WB coil 24a and to output them to the corresponding reception circuits 30d. In other words, the switch composition unit 30c is configured so that, in conformance with the number of the reception circuits 30d, the composition processing and switching with respect to NMR signals received from the coil elements 24c or the WB coil 24a are performed in the switch composition unit 30c, and that NMR signals can be received from various imaging areas by forming sensibility distributions in response to the imaging areas, using a plurality of desired coil elements 24c.

However, NMR signals may be received by WB coil 24a alone without providing the coil elements 24c. Also, NMR signals received in the coil elements 24c or the WB coil 24a may be directly outputted to the reception circuits 30d without providing the switch composition unit 30c. Furthermore, more coil elements 24c may be extensively arranged.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex data obtained through the detection of a NMR signal and A/D (analog to digital) conversion to the NMR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

In addition, an ECG unit 38 for acquiring an ECG (electro cardiogram) signal of the object P is provided with the magnetic resonance imaging apparatus 20. The ECG signal detected by the ECG unit 38 is outputted to the computer 32 through the sequence controller 31. Note that, a PPG (peripheral pulse gating) signal representing a beat as pulse wave information may be acquired instead of an ECG signal representing a beat as heart rate information.

The computer 32 gets various functions by the operation unit 35 executing some programs stored in the storage unit 36 of the computer 32. Alternatively, some specific circuits having various functions may be provided with the magnetic resonance imaging apparatus 20 instead of using at least some of the programs.

Figure 3:
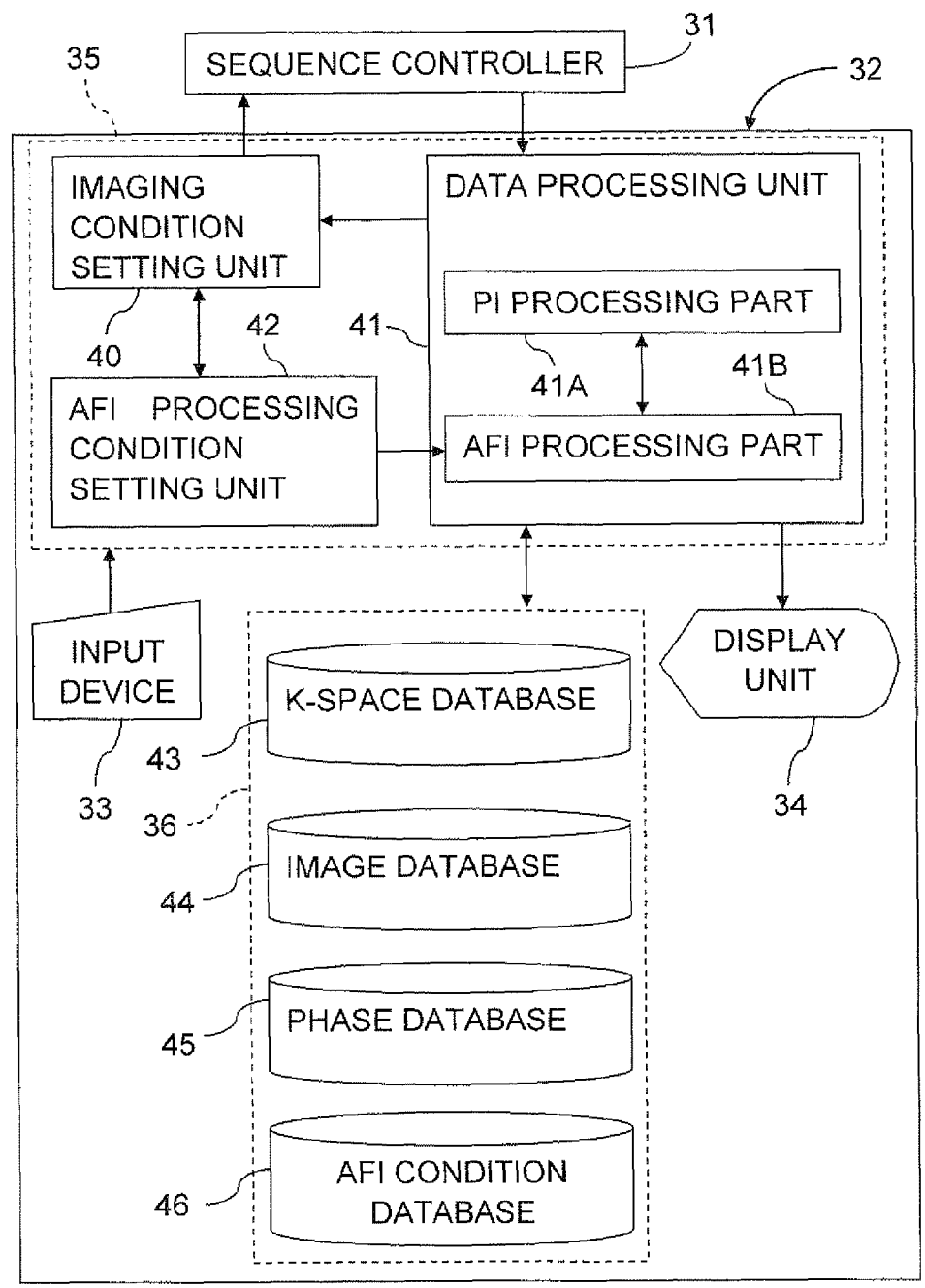
FIG. 3 is a functional block diagram of the computer shown in FIG. 1.

FIG. 3 is a functional block diagram of the computer 32 shown in FIG. 1.

The operation unit 35 of the computer 32 functions as an imaging condition setting unit 40, a data processing unit 41 and an AFI processing condition setting unit 42 by performing the programs stored in the storage unit 36. In addition, the storage unit 36 functions as a k-space database 43, an image database 44, a phase database 45 and an AFI condition database 46. The data processing unit 41 includes a PI (parallel imaging) processing part 41A and an AFI processing part 41B.

The imaging condition setting unit 40 has a function to set imaging conditions including a pulse sequence based on instruction from the input device 33 and control the sequence controller 31 to drive the sequence controller 31 by outputting the set imaging conditions to the sequence controller 31.

Especially, the imaging condition setting unit 40 is configured to be able to set imaging conditions for AFI in which MR data is sampled asymmetrically in the wave number direction in k-space and imaging conditions for PI in which MR data is received with plural coil elements 24c. AFI and PI can be applied to various imaging including MRA (magnetic resonance angiography) and DWI (diffusion weighted imaging). In AFI, MR data corresponding to a sampling region asymmetric in the wave number direction in k-space is acquired from the object P.

Note that, PI has types like SENSE (Sensitivity Encoding), SMASH (Shimadzu minimum angle shot) and GRAPPA (generalized autocalibrating partially parallel acquisition). In SENSE, data processing is performed in r-space. On the contrary, data is processed in k-space in SMASH. GRAPPA is a developed SMASH. In GRAPPA, unfolding processing, which is post processing specific to PI, and image reconstruction processing are performed to k-space data corresponding to each of the coil elements 24c and subsequently respective pieces of image data corresponding to the coil elements 24c after unfolding processing are mutually combined.

The imaging conditions for AFI include a sampling region $(-K_c \leq k \leq K_{max})$ in the wave number direction in one direction k of the readout direction and the phase encode direction of k-space data for 2D (two dimensional) sampling. The border $K_c$ of the sampling region can be set as a variable value according to setting information from the AFI processing condition setting unit 42, for example. The region where no data is sampled may be in the positive side or the negative side in the k direction. Here, the explanation is made with an example case where the non-sampling region is in the negative side.

Alternatively, the border $K_c$ of the sampling region can be determined based on data acquired by a pre-scan. In this case, conditions for data acquisition by the pre-scan are set in the imaging condition setting unit 40. Specifically, a condition for MR data acquisition with gradually changing the border $K_c$ of the sampling region is set as one for the pre-scan.

Figure 4:
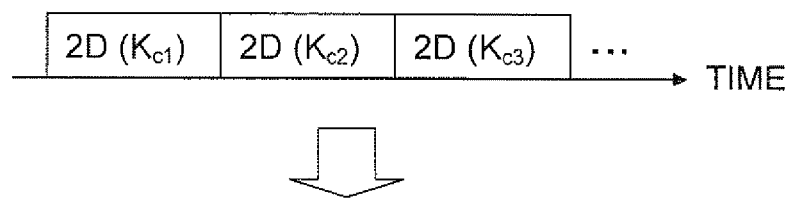
FIG. 4 is a diagram explaining a method of determining the border of data sampling region in AFI by a pre-scan.
Figure 4:
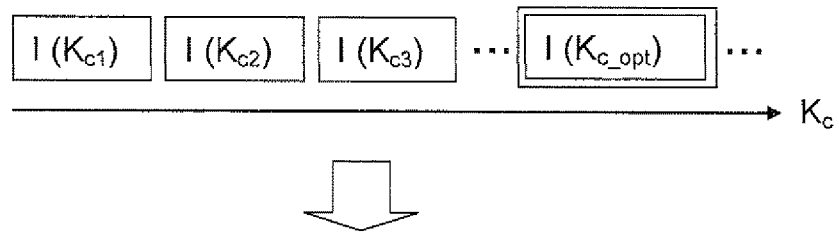
Figure 4:
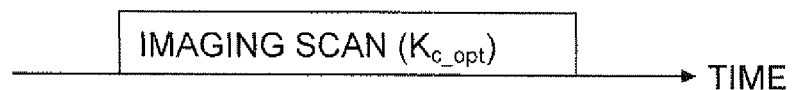

FIG. 4 is a diagram explaining a method of determining the border of data sampling region in AFI by a pre-scan;

As shown in FIG. 4 (A), a condition for performing data acquisition with gradually changing the border $K_c$ of the data sampling region into $K_{c1}$, $K_{c2}$, $K_{c3}$, . . . is set for the pre-scan. Hereinafter, the pre-scan for determining the border $K_c$ is referred to as a Kc-PREP scan. Matching conditions for data acquisition by a Kc-PREP scan with that by an imaging scan as much as possible leads to obtain a more appropriate border $K_c$. On the other hand, the border $K_c$ of the data sampling region may be changed with setting the phase encode to zero to acquire 1D (one-dimensional) projection data for shortening data acquisition period.

When AFI processing described later is performed to pieces of asymmetric sampling data acquired by the Kc-PREP scan, frames of 2D image data I ($K_{c1}$), I ($K_{c2}$), I ($K_{c3}$), . . . corresponding to mutually different borders $K_{c1}$, $K_{c2}$, $K_{c3}$, . . . of the data sampling region respectively are generated as shown in FIG. 4 (B). Consequently, the image I ($K_{c\_opt}$) having the optimum image quality can be selected by information for image selection through the input device 33 form a user or image processing such as threshold processing. Then, the border $K_{c\_opt}$ of the data sampling region corresponding to the image I ($K_{c\_opt}$) having the optimum image quality can be determined as an imaging condition for an imaging scan and an AFI data processing condition based on the information for selecting one frame of image data from the frames of image data.

After that, the imaging scan is performed with setting the selected border $K_{c\_opt}$ of the data sampling region as an imaging condition as shown in FIG. 4 (C).

Further, the imaging condition setting unit 40 has a function to set other imaging conditions for an imaging scan and a condition for data acquisition by a pre-scan for acquiring data necessary for processing of data acquired by an imaging scan. For example, for shimming the static magnetic field, conditions for data acquisition by a pre-scan for shimming the static magnetic field are set. By using MR data acquired by a pre-scan for shimming the static magnetic field, a map of magnetic field distribution is measured to determine current to be supplied to the shim coil 22 from the shim coil power supply 28. As another example, a pre-scan is performed to measure a sensitivity map of coil elements 24c necessary for unfolding processing of data acquired by PI.

The data processing unit 41 has functions to obtain raw data acquired under the conditions for AFI and PI from the sequence controller 31 to arrange the raw data in k-space formed in the k-space database 43 as k-space data and generate image data for diagnosis by AFI processing of the k-space data and PI processing due to PI. AFI processing is a processing to generate image data, equivalent to one generated from symmetrically sampled data, based on k-space data sampled asymmetrically in the wave number direction in k-space with phase correction processing. Specifically, the AFI processing is a processing for generating image data base on symmetrically sampled MR data by data processing including phase correction and filter processing for obtaining complex conjugate. The pieces of image data for diagnosis generated by PI processing and AFI processing can be displayed on the display unit 34.

The PI processing part 41A in the data processing unit 41 has a function to perform PI processing. On the other hand, the AFI processing part 41B has a function to perform AFI processing. In PI processing and AFI processing, transformation between k-space data and r-space data is often required. Accordingly, a function to perform transformation processing between k-space data and r-space data is provided with the PI processing part 41A and the AFI processing part 41B as well as functions to read k-space data from the k-space database 43, write k-space data to the k-space database 43, read r-space data from the image database 44 and write r-space data to the image database 44.

Therefore, k-space data is stored in the k-space database 43. Meanwhile, r-space data is stored in the image database 44.

PI processing includes unfolding processing to unfold image data having aliasing to remove the aliasing and compound processing to combine pieces of image data for coil elements 24c. On the other hand, AFI processing filter processing of k-space data to compensate data using complex conjugate symmetry, phase correction processing of r-space data and processing to reduce error in the phase correction.

Figure 5:
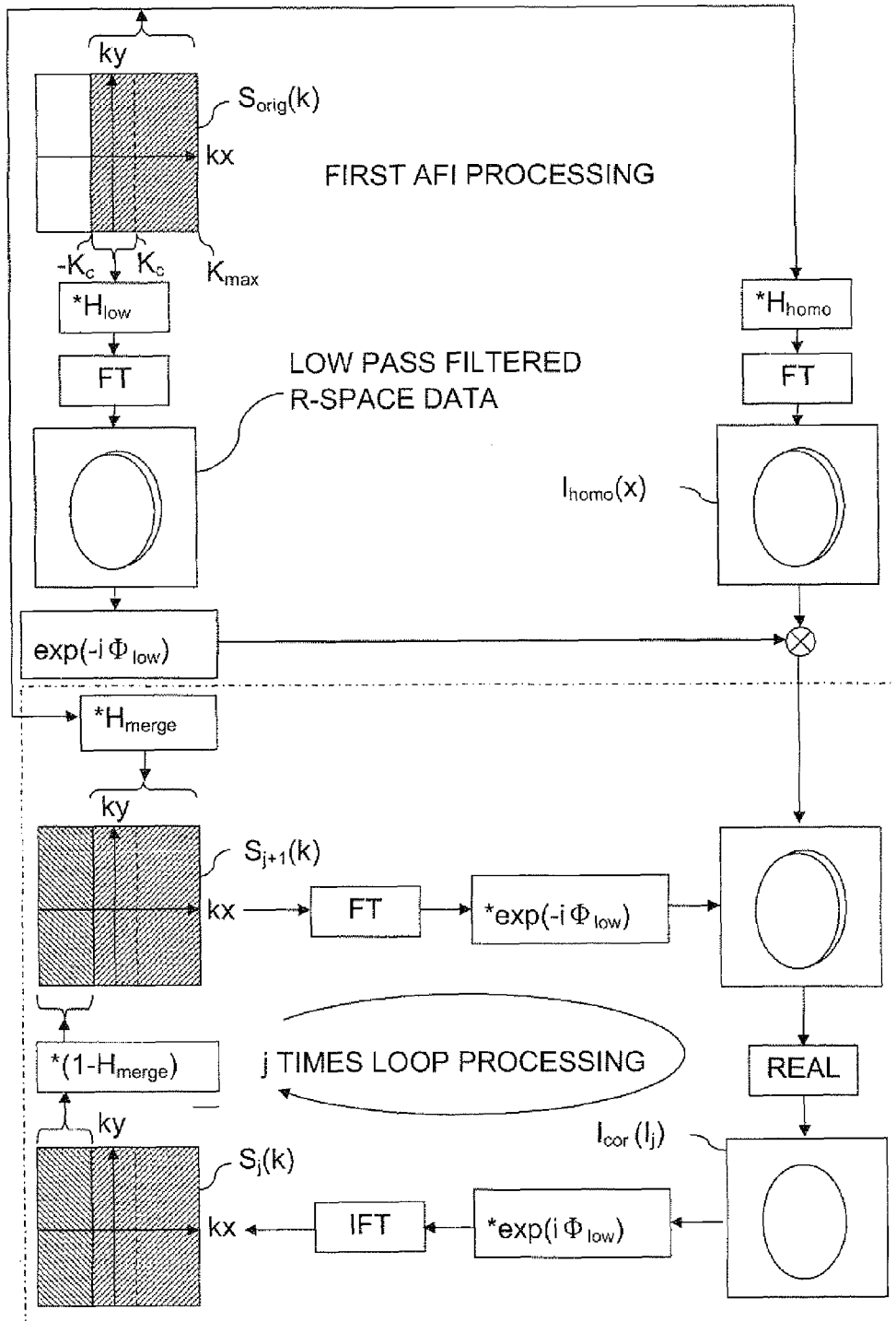
FIG. 5 is a diagram showing an example of the first AFI processing performed by the data processing unit shown in FIG. 3.

FIG. 5 is a diagram showing an example of the first AFI processing performed by the data processing unit 41 shown in FIG. 3.

FIG. 5 shows an example of k-space data sampled asymmetrically in the kx direction of k-space. However, the same applies to k-space data sampled asymmetrically in the ky direction. Further, 3D (three-dimensional) k-space data sampled asymmetrically in the 2D directions can be subjected to AFI processing. Hereinafter, explanation is made with an example case of 1D asymmetric sampling data in the k direction to ease the explanation.

Note that, determining the direction, in which data is asymmetrically sampled, to the readout direction makes it possible to shorten the TE (echo time). Alternatively, determining the direction, in which data is asymmetrically sampled, to an encode direction makes it possible to shorten the imaging period.

As shown in FIG. 5, MR data is acquired into k-space so as to be asymmetric with regard to the center and subsequently is arranged as k-space data in k-space in AFI method. Therefore, a sampling region asymmetric with regard to k=0 is formed in k-space and filled with partial k-space data FIG. 5 shows an example of arranging k-space data within a 1D range of $-K_c \leq k \leq K_{max}$ in the abscissa axis direction, ie., k-space data of which data in one high frequency side lacks, as partial original k-space data $S_{orig}(k)$ In the first AFI processing, the partial original k-space data $S_{orig}(k)$ ($-K_c \leq k \leq K_{max}$) is subjected to a homodyne filter $H_{homo}(k)$ and subsequently FT to generate original r-space data $I_{homo}(x)$ as shown by equation (1) at the first.

The homodyne filter is equivalent to a filter filling a part having no data in k-space with complex conjugate data. That is, compensation processing of k-space data using symmetry in complex conjugate is performed by windowing the partial original k-space data $S_{orig}(k)$ with the homodyne filter. The homodyne filter becomes a window function having mutually different weights between the symmetric sampling part and the asymmetric sampling part of k-space data.

$$I_{homo}(x)=FT\{H_{homo}(k)S_{orig}(k)\} \quad (1)$$

Meanwhile, a LPF (low pass filter) $H_{low}(k)$ is applied to the partial original k-space data $S_{orig}(k)$ to extract original k-space data $S_{low}(k)$ ($-K_c \leq k \leq K_c$) in a low frequency region symmetric in k-space as shown by equation (2). Subsequently, the extracted original k-space data $S_{low}(k)$ in the low frequency region is subjected to FT to generate low-pass filtered r-space data $I_{low}(x)$ corresponding to low frequency data.

$$I_{low}(x)=FT\{H_{homo}(k)S_{orig}(k)\} \quad (2)$$

Next, a phase distribution $\Phi_{low}(x)$ in the low frequency region is calculated based on the low-pass filtered r-space data $I_{low}(x)$, a phase correction is performed to the original r-space data $I_{homo}(x)$ with the phase distribution $\Phi_{low}(x)$ in the low frequency region and subsequently real processing for removing the imaginary part is performed to the original r-space data $I_{homo}(x)$ after the phase correction as shown by equations (3-1) and (3-2). Consequently, r-space data $I_{cor}(x)$ after AFI processing is generated.

$$exp\{-i\Phi_{low}(x)\}=I_{low}*(x)/abs\{I_{low}(x)\} \quad (3\text{-}1)$$

$$I_{cor}(x)=Re[I_{homo}(x)exp\{-i\Phi_{low}(x)\}] \quad (3\text{-}2)$$

wherein Re[ ] in equation (3-2) represents a function which outputs the real part of a complex number.

That is, a phase distribution cannot be ignored in practice and therefore symmetry in complex conjugate is not be kept due to the imaginary part which does not become zero though AFI is an imaging method in which k-space data is filled in a part having no sampling data using the symmetry in complex conjugate. Accordingly, a phase correction is performed based on a phase distribution to keep the symmetry in complex conjugate. However, correction errors sometimes occur in spite of the phase correction.

For that reason, loop processing for reducing errors in the phase correction is performed to the r-space data $I_{cor}(x)$ after the phase correction a predetermined number of times. The loop processing is based on the principle that the imaginary part of the r-space data $I_{cor}(x)$ after the phase correction becomes zero if no error occurs in the phase correction since the complex conjugate in k-space becomes symmetric. Therefore, the loop processing is a convergence calculation to converge the imaginary part of the r-space data $I_{cor}(x)$ into zero. The convergence calculation which repeats the loop processing reduces errors in the phase correction occurring due to the homodyne filter processing.

Specifically, the r-space data $I_{cor}(x)$ having only the real part after the phase correction is set as the initial r-space data $I_j(x)$ in the loop processing and processing for returning the phase of the r-space data $I_j(x)$ having only the real part into one before the phase correction is performed as shown by equation (4). Consequently, the r-space data $I'_j(x)$ of which phase is returned is generated.

$$I'_j(x)=I_j(x)exp\{i\Phi_{low}(x)\} \quad (4)$$

Next, the r-space data $I'_j(x)$, of which phase has been returned, after the processing for returning the phase is transformed into the k-space data $S_j(k)$ by IFT as shown by equation (5).

$$S_j(k)=IFT\{I'_j(x)\} \quad (5)$$

Next, the range $-K_c \leq k \leq K_{max}$ which is a part of the k-space data $S_j(k)$ is substituted for the k-space data extracted from the partial original k-space data $S_{orig}(k)$ by a data extracting filter $K_{merge}(k)$ as shown by equation (6). In other words, the k-space data within the range of $k<-K_c$ out of the k-space data $S_j(k)$ obtained by equation (5) is merged with the k-space data within the range of $-K_c \leq k \leq K_{max}$ out of the partial original k-space data $S_{orig}(k)$.

$$S_{j+1}(k)=H_{merge}(k)S_{orig}(k)+\{1-H_{merge}(k)\}S_j(k) \quad (6)$$

Next, the phase correction is performed to the r-space data obtained by FT of the merged k-space data $S_{j+1}(k)$ obtained by equation (6) and subsequently real processing for removing the imaginary part of the r-space data after the phase correction is performed. Specifically, by processing for transforming the k-space data $S_{j+1}(k)$ after the substitution and composition into r-space data to perform the phase correction and processing for obtaining the real part of the r-space data after the phase correction, the r-space data $I_{j+1}(x)$ having only the real part after the phase correction is generated again as shown by equation (7).

$$I_{j+1}(x)=Re[FT\{S_{j+1}(k)\}exp\{-i\Phi_{low}(x)\}] \quad (7)$$

The loop processing from equation (4) to equation (7) is repeated with setting j=0, 1, 2, 3, . . . until the predetermined convergence condition is satisfied. That is, a convergence calculation to converge the imaginary part of the r-space data, which is to be subjected to the processing for obtaining the real part, into zero is performed. The convergence condition can be set to a case where a difference between the j-th r-space data $I_j(x)$ and (j+1)-th r-space data $I_{j+1}(x)$ becomes under a threshold $E_{th}$ as shown by equation (8) for example.

$$|I_{j+1}(x)-I_j(x)|<E_{th} \qquad (8)$$

Then, repeating the loop processing until the convergence condition is satisfied generates the r-space data I(x) as diagnostic image data. Hence, when the loop processing is repeated j times, FT is performed (2+j) times while IFT is performed j times in the first AFI processing. Consequently, a data processing period in the first AFI processing becomes a processing period including time necessary for 2+j FTs and j IFTs.

Figure 6:
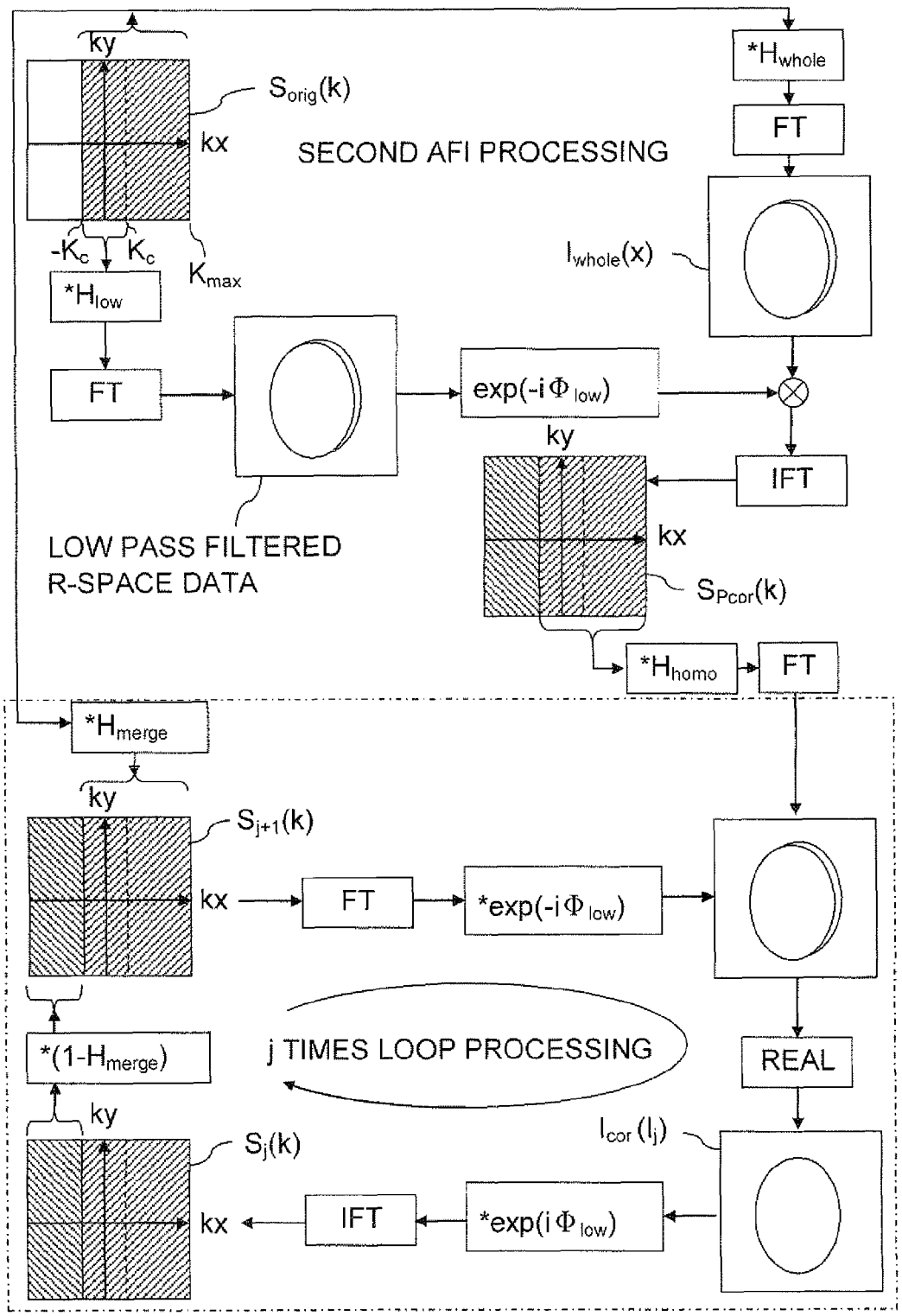
FIG. 6 is a diagram showing an example of the second AFI processing performed by the data processing unit shown in FIG. 3.

FIG. 6 is a diagram showing an example of the second AFI processing performed by the data processing unit 41 shown in FIG. 3.

The second AFI processing shown in FIG. 6 is mainly different from the first AFI processing in the point that the phase correction is performed before the homodyne filter $H_{homo}(k)$ is applied to the partial original k-space data $S_{orig}(k)$. Therefore, explanations for the processing equivalent to that in the first AFI processing are omitted.

Also in the second AFI processing, the low-pass filtered r-space data $1_{low}(x)$ corresponding to low frequency data is generated from the partial original k-space data $S_{orig}(k)$ by equation (2) like the first AFI processing.

Meanwhile, asymmetric original k-space data is extracted by a filter $H_{whole}$ for extracting data in the whole frequency region from the partial original k-space data $S_{orig}(k)$ and original r-space data $I_{whole}(x)$ is generated by FT of the extracted asymmetric original k-space data as shown by equation (9).

$$I_{whole}(x)=FT\{H_{whole}S_{orig}(k)\} \qquad (9)$$

Next, the phase correction of the original r-space data $I_{whole}(x)$ is performed using a phase distribution $\Phi_{low}(x)$ in a low frequency region obtained from the low-pass filtered r-space data $I_{low}(x)$ as shown by equation (10). Consequently, the r-space data $I_{pcor}(x)$ after the phase correction is obtained.

$$I_{pcor}(x)=I_{whole}(x)exp\{-i\Phi_{low}(x)\} \qquad (10)$$

Next, the r-space data $I_{pcor}(x)$ after the phase correction is transformed by IFT into the k-space data $S_{Pcor}(k)$ after the phase correction as shown by equation (11).

$$S_{Pcor}(k)=IFT\{I_{pcor}(x)\} \qquad (11)$$

Next, the k-space data $S_{Pcor}(k)$ after the phase correction is subjected to the homodyne filter $H_{homo}(k)$ and subsequently transformed into the r-space data by FT and real processing for removing the imaginary part of the r-space data is performed as shown by equation (12). Consequently, the r-space data $I_{cor}(x)$ after the phase correction and the homodyne filter processing is generated.

$$I_{cor}(x)=Re[FT\{H_{homo}(k)S_{Pcor}(k)\}] \qquad (12)$$

Next, the loop processing is performed to the r-space data $I_{cor}(x)$ after the phase correction generated as described above the predetermined times like the first AFI processing. Therefore, when the loop processing is repeated j times in the second AFI processing, FT is performed (3+j) times while IFT is performed (1+j) times. Hence, the data processing period in the second MI processing becomes longer than that in the first AFI processing by a period corresponding to a single FT and MT. However, the phase correction processing is performed before the homodyne filter $H_{homo}(k)$ is applied to the partial original k-space data $S_{orig}(k)$. Therefore, the second AFI processing can reduce errors in the phase correction due to the homodyne filter processing more than the first AFI processing.

Figure 7:
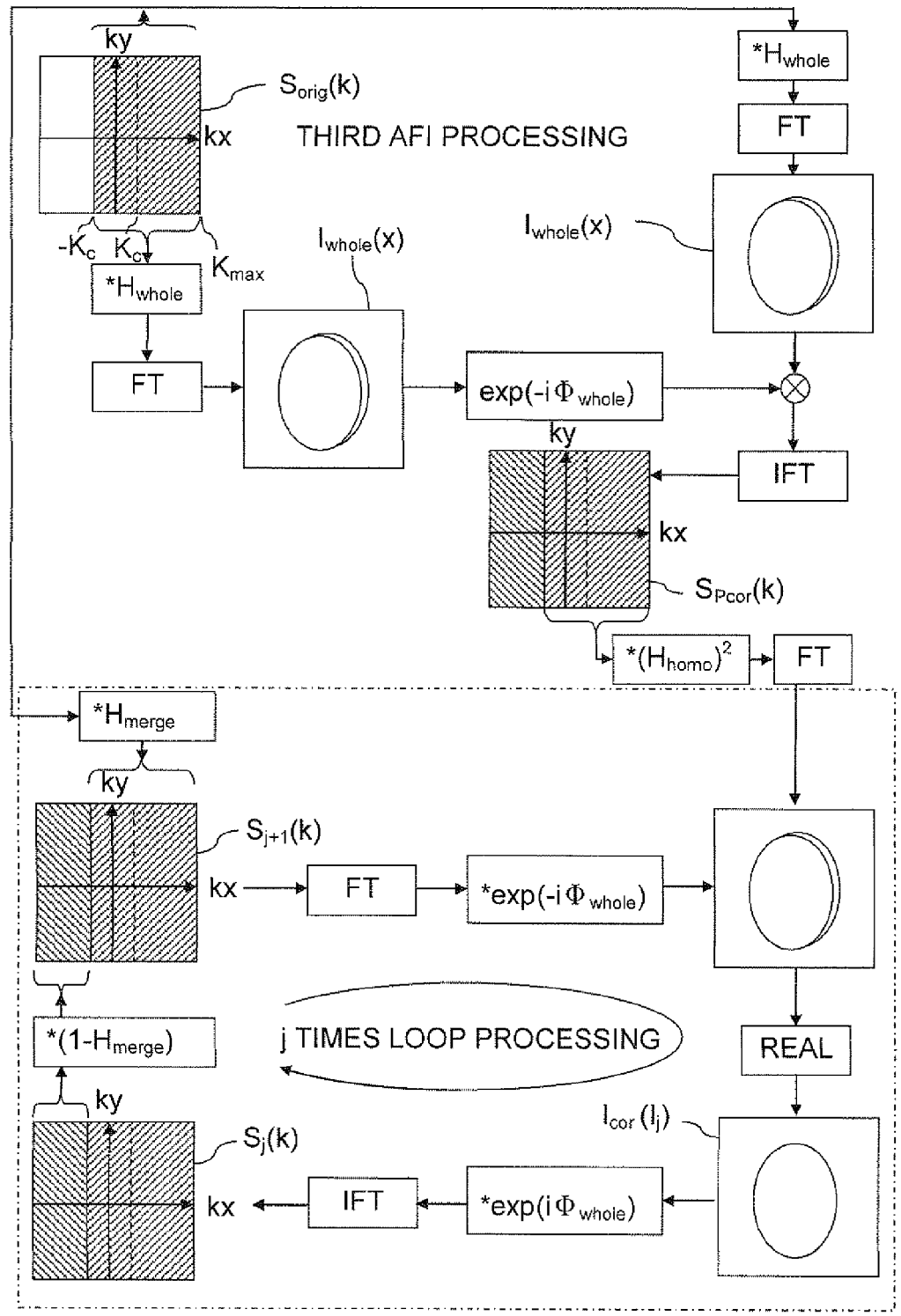
FIG. 7 is a diagram showing an example of the third AFI processing performed by the data processing unit shown in FIG. 3.

FIG. 7 is a diagram showing an example of the third AFI processing performed by the data processing unit 41 shown in FIG. 3.

The third AFI processing shown in FIG. 7 is different from the second AFI processing in the point that a phase distribution $\Phi_{whole}(x)$ in the whole frequency region is estimated based on the entire partial original k-space data $S_{orig}(k)$ sampled asymmetrically and subsequently the phase correction is performed using the phase distribution $\Phi_{whole}(x)$ in the whole frequency region. That is, the phase distribution $\Phi_{whole}(x)$ in the whole frequency region is estimated for the phase correction by using not only the symmetrically sampled part but also the asymmetrically sampled part of the partial original k-space data $S_{orig}(x)$. The other points are similarly to those in the second AFI processing, and therefore, detail explanations thereof are omitted.

In the third AFI processing, the phase distribution $\Phi_{whole}(x)$ in the whole frequency region is used for the phase correction. Therefore, the third AFI processing can reduce errors in the phase correction much more than the second AFI processing. Note that, FT is performed (3+j) times while IFT is performed (1+j) times in the third AFI processing.

In the AFI processing methods described above, the phase distribution for the phase correction is estimated from the k-space data self to be a correction target. However, the phase distribution for the phase correction can be obtained based on MR data other than that for generating diagnostic image data in advance.

Especially, k-space data in a frequency region wider than that of the k-space data sampled asymmetrically for generating the diagnostic image data can be obtained by data acquisition without the AFI method. For example, acquiring k-space data in the whole frequency region makes it possible to obtain a phase distribution $\Phi_{whole}(x)$ in the entire frequency region. Therefore, the phase correction can be performed with a phase distribution obtained based on other MR data which is different from the MR data for generating image data by the AFI method and is acquired in a frequency region larger than that for the MR data for generating image data by the AFI method.

In case of obtaining the phase distribution based on not the self data but other data, it is practical to obtain the phase distribution based on data acquired from the same imaging part of the same object in view of accuracy. That is, a phase distribution closer to original one can be estimated. In this case, it is important to sample the other data up to a higher frequency region than the frequency region of the self data at least.

For example, approximately full-sampled k-space data can be acquired by a shimming sequence for measuring a magnetic field map for shimming the static magnetic field. Alternatively, data corresponding to a frequency region in k-space wider than that of the self data is acquired by a pre-scan for measuring a sensitivity distribution of coil elements 24c for PI processing. Therefore, the phase distribution in the whole frequency region can be obtained for the phase correction using data acquired by a shimming sequence or a sequence for acquiring a sensitivity map. That is, the phase correction can be performed with a phase correction obtained based on MR data acquired by a pre-scan for measuring a magnetic field map for shimming the static magnetic field or a pre-scan for measuring sensitivity distributions of coil elements 24c.

Accordingly, functions to obtain a phase distribution for the phase correction based on other data acquired by a desired scan such as a pre-scan, to write the obtained phase distribution to the phase database 45 and to read a phase distribution from the phase database 45 are provided with the AFI processing part 41B. Therefore, a previously obtained phase distribution for the phase correction in the AFI processing is stored in the phase database 45.

When the phase distribution is obtained based on data other than the self data, both the other data and the self data may be used for obtaining the phase distribution. For example, if an index representing a similarity between a phase shift in the other data according to a sequence and that in the data to be the target of the phase correction is not lower than a threshold, a phase distribution in the whole frequency region obtained based on the other data can be used as the phase distribution for the phase correction. On the contrary, if the index representing the similarity between the phase shifts is lower than the threshold, data in a part, which is not be sampled in the self data to be the target of the phase correction, out of the almost fully sampled other k-space data is extracted by windowing the other k-space data. Then, the extracted k-space data is transformed into r-space data, and subsequently, a phase distribution calculated base on the obtained r-space data is merged with a phase distribution calculated based on the self data.

Consequently, a phase distribution map in the whole frequency region based on both the other data and the self data can be obtained. Such a calculation method of the phase distribution can reduce errors in the phase correction though a phase distribution different from the proper one is used for the phase correction exactly.

Note that, the above-mentioned example adopts the phase correction performed to k-space data. However, the phase correction may be performed to r-space data.

By the way, the order of the PI processing and the AFI processing can be optimized to shorten the processing period. For that purpose, the PI processing part 41A and the AFI processing part 41B are respectively configured to give intermediate data on or after processing to each other. For example, homodyne filter processing in the AFI processing is performed to the respective pieces of k-space data corresponding to the plural coil elements 24c, and after that, unfolding processing and compound processing of image data in the PI processing is performed. In this case, the target of the loop processing for reducing errors in the phase correction is a single piece of r-space data. In other words, if the AFI loop processing is performed after unfolding processing and compound processing of image data in the PI processing, the target of the loop processing is only image data merged between the coil elements 24c. Therefore, the number of repetitions of the loop processing can be reduced to decrease the total amount and period of data processing.

Meanwhile, the AFI processing condition setting unit 42 has a function to set conditions for the AFI processing to appropriate conditions according to a phase distribution used for the phase correction processing or image ones influencing the phase distribution. The conditions for the AFI processing, which are set according to a phase distribution used for the phase correction or imaging conditions influencing the phase distribution, include not only the type of the AFI processing, the number j of repetition of the loop processing and the border $K_c$ of the sampling region as described above but also a strength and shape of the homodyne filter and so on. The strength of the homodyne filter becomes a gain for asymmetrically sampled. MR signals.

Note that, frames of 2D image data generated by a Kc-PREP scan for acquiring MR data with gradually changing the border $K_c$ of the sampling region have image qualities according to the phase distribution used for the phase correction and the imaging conditions influencing the phase distribution. Therefore, setting the border $K_c$ of the sampling region though a selection of a frame of 2D image data having an appropriate image quality is setting an appropriate border $K_c$ of the sampling region according to the phase distribution used for the phase correction or imaging conditions influencing the phase distribution.

The type of the AFI processing can be specified by parameterizing three alternative matters for example. The first alternative matter is whether the phase correction processing is performed before or after the homodyne filter processing. The second alternative matter is whether a phase distribution $\Phi_{whole}(x)$ in the whole frequency region corresponding to a data processing range is used for the phase correction or a phase distribution $\Phi_{low}(x)$ in a low frequency region corresponding to a symmetric part of an asymmetric sampling region is used for the phase correction. The third alternative matter is whether the phase distribution $\Phi(x)$ used for the phase correction is estimated based on only self data which is k-space data self to be corrected, only data other than the self data or both the self data and the other data.

The all kinds of parameters specifying the conditions for the data processing in AFI can be set as variable values according to a phase distribution used for the phase correction or imaging conditions each influencing the phase distribution by inputting setting information into the AFI processing condition setting unit 42 with operation of the input device 33. Further, plural sets of conditions for the AFI processing can be prepared as alternatives corresponding to phase distributions or imaging conditions so that one alternative can be selected with operation of the input device 33. Alternatively, plural imaging protocols corresponding to various imaging conditions can be related with exclusive and appropriate parameter sets for the AFI processing respectively and the related parameter sets can be stored.

The AFI condition database 46 stores data processing conditions for AFI corresponding to plural imaging conditions or alternatives of data processing conditions for AFI according to plural imaging conditions, determined by simulations or experientially in advance. Meanwhile, the AFI processing condition setting unit 42 is configured to obtain the data processing condition for AFI or the alternative of data processing condition for AFI, which corresponds to imaging conditions influencing the phase distribution, from the AFI condition database 46 as a storage unit when the AFI processing condition setting unit 42 receives information representing an imaging condition such as information specifying a selected imaging protocol from the imaging condition setting unit 40. In this case, selection of an imaging protocol with operation of the input device 33 automatically sets corresponding parameters specifying the AFI processing conditions without conscious of a user for example. Therefore, convenience of users can be improved.

On the other hand, the border $K_c$ of the sampling region may be determined by performing a Kc-PREP scan as described above.

The imaging conditions influencing the phase distribution include a type of imaging sequence, a TE and an imaging part. For example, imaging with a FE (field echo) sequence such as a FASE (fast advanced spin echo or fast asymmetric spin echo) sequence, a GE (gradient echo) sequence having a long TE, an EPI (echo planar imaging) sequence or a SSFP (steady state free precession) sequence often causes a remarkable artifact due to errors in the phase correction.

In addition, MRA of which imaging part are blood vessels, DWI and imaging by a magnetic resonance imaging apparatus forming a strong magnetic field require a phase correction with a high accuracy. MRA includes FS-BB (flow-sensitive black-blood) method, TOF (time of flight) method and the like. The FS-BB method is one of BB (black blood) method by which blood is depicted blackly as a low signal region. Specifically, a MPG (motion probing gradient) pulse is applied as a dephase gradient pulse to decrease signals from blood in a ROI (region of interest) selectively in the FS-BB method. Therefore, a phase of blood is positively dispersed, i.e., the blood is dephased in the FS-BB method.

Accordingly, imaging under these conditions each requiring a phase correction at a high accuracy generates a remarkable artifact due to possible errors in the phase correction. For that reason, setting a more appropriate API processing conditions specialized in each imaging condition can improve effect in reduction of artifacts.

Next, example cases of determining appropriate parameters specifying the AFI processing conditions by a simulation will be described. Firstly, an example of determining a type of the AFI processing will be described.

Figure 8:
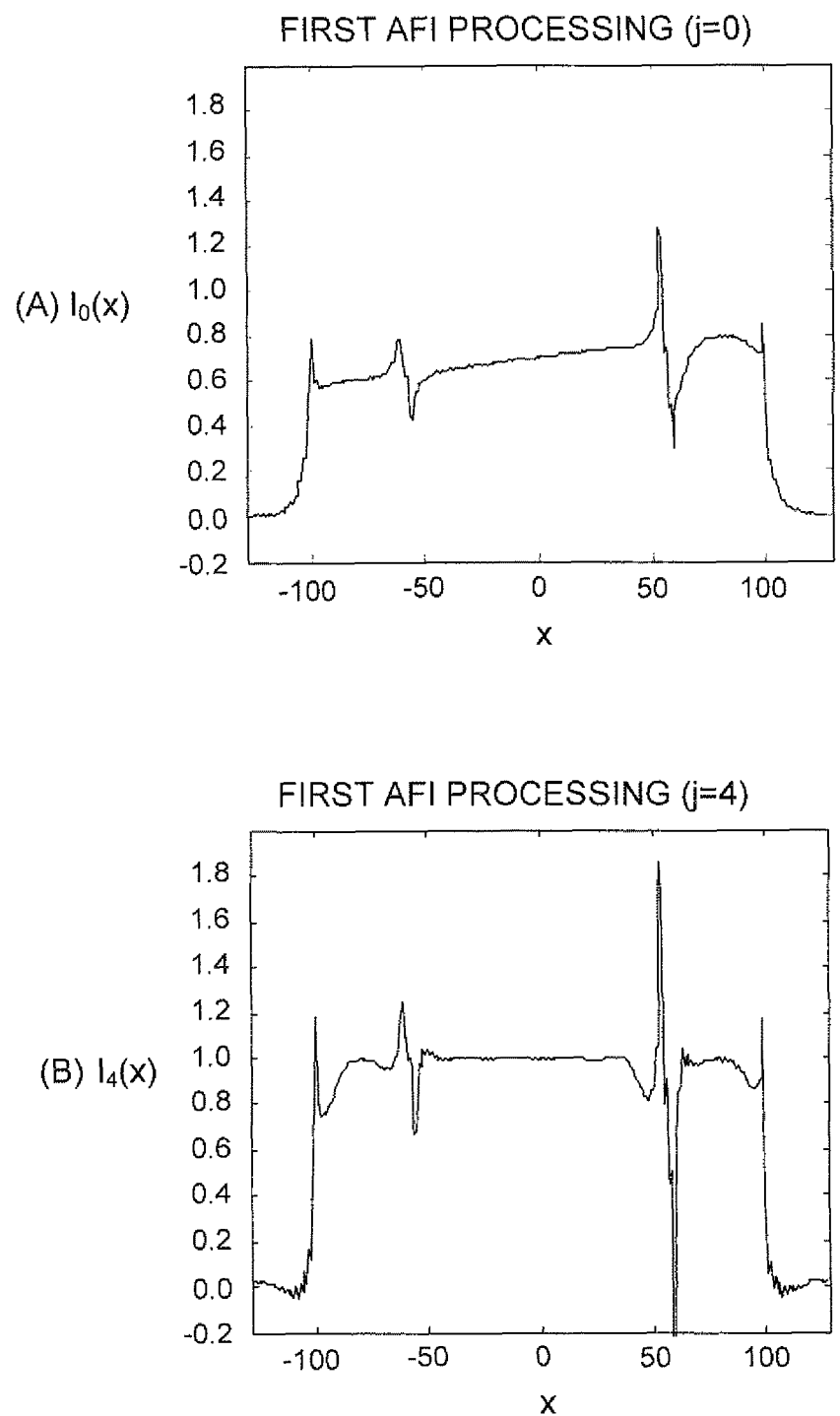
FIG. 8 shows an example of r-space data I(x) generated by the first AFI processing in a one-dimensional simulation.
Figure 9:
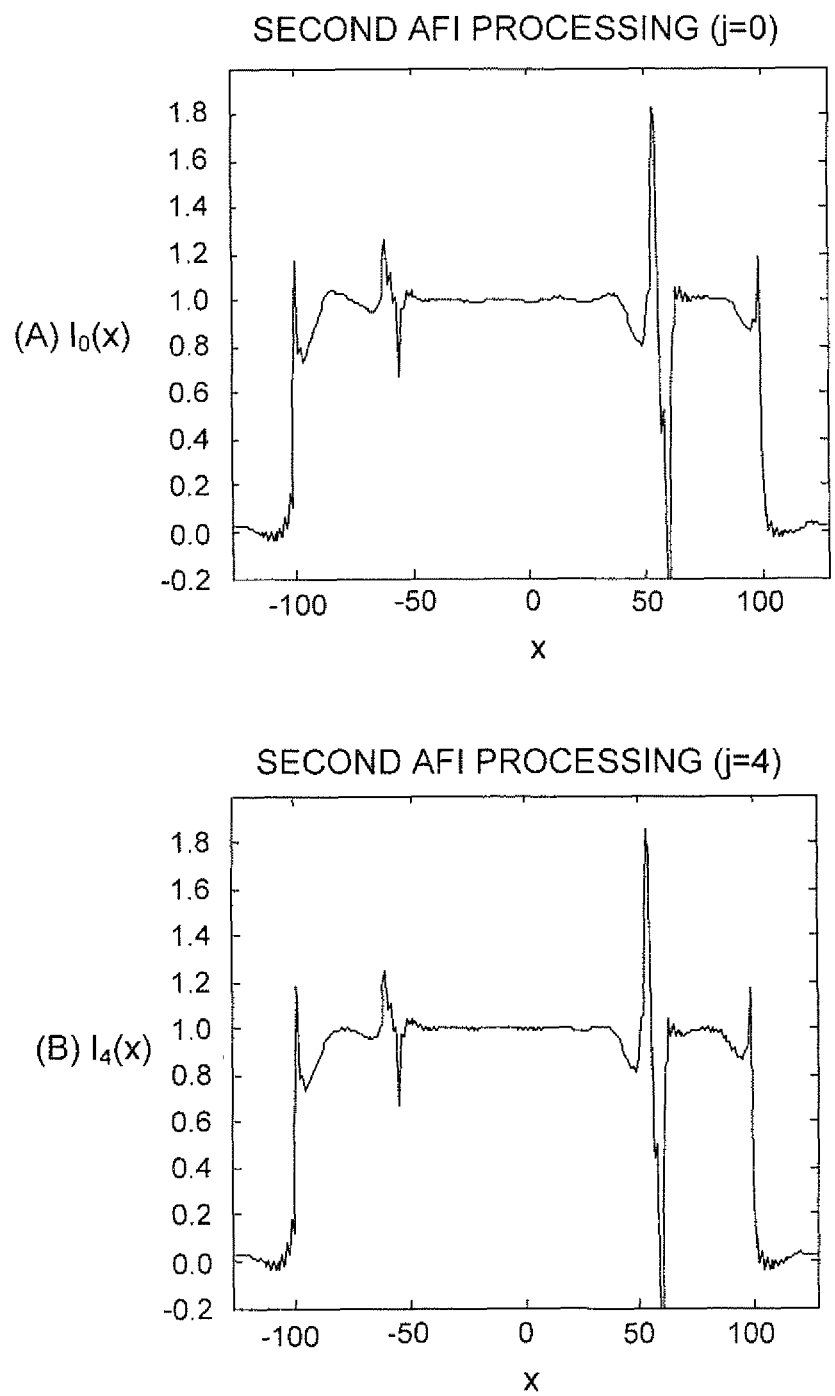
FIG. 9 shows an example of r-space data I(x) generated by the second AFI processing in a one-dimensional simulation.
Figure 10:
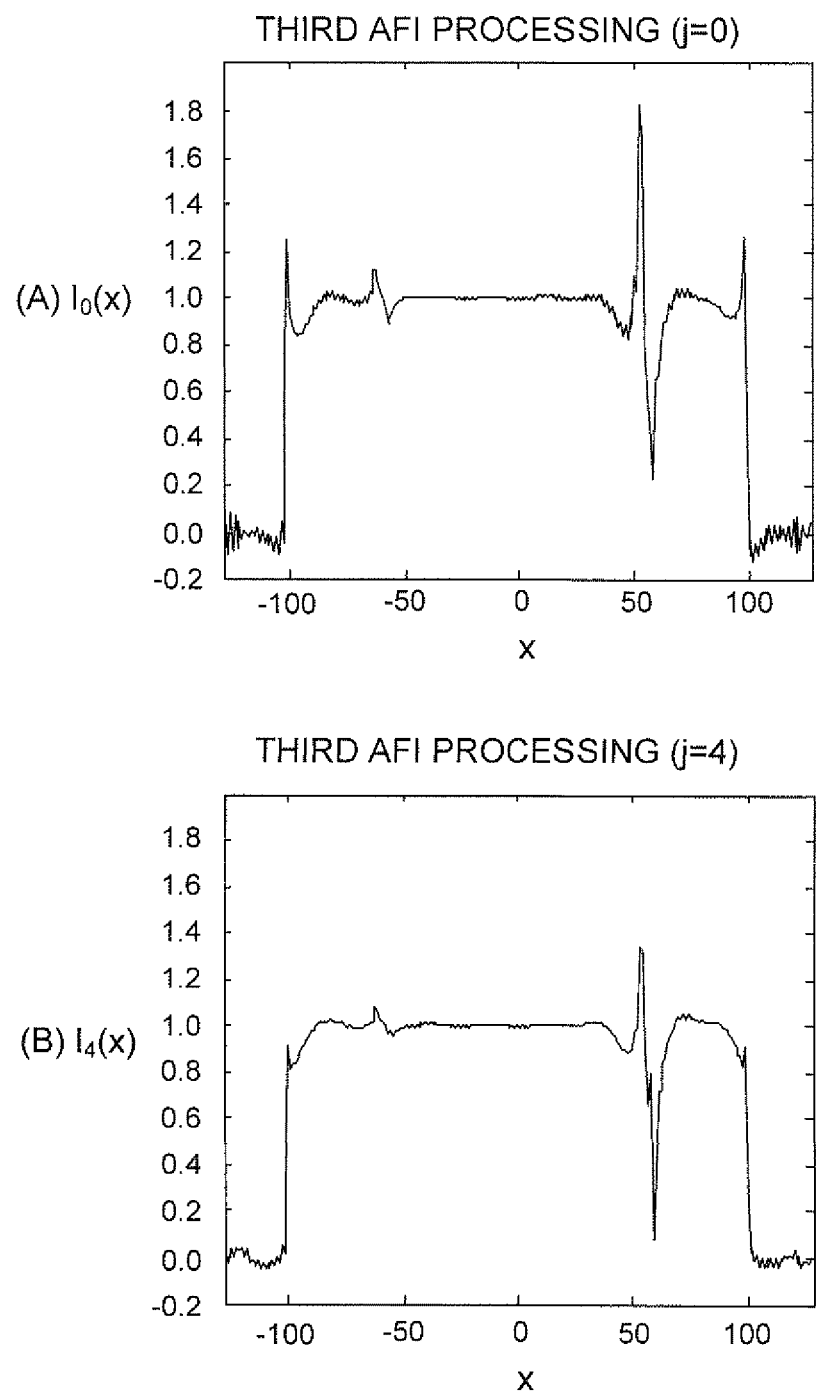
FIG. 10 shows an example of r-space data I(x) generated by the third AFI processing in a one-dimensional simulation.
Figure 11:
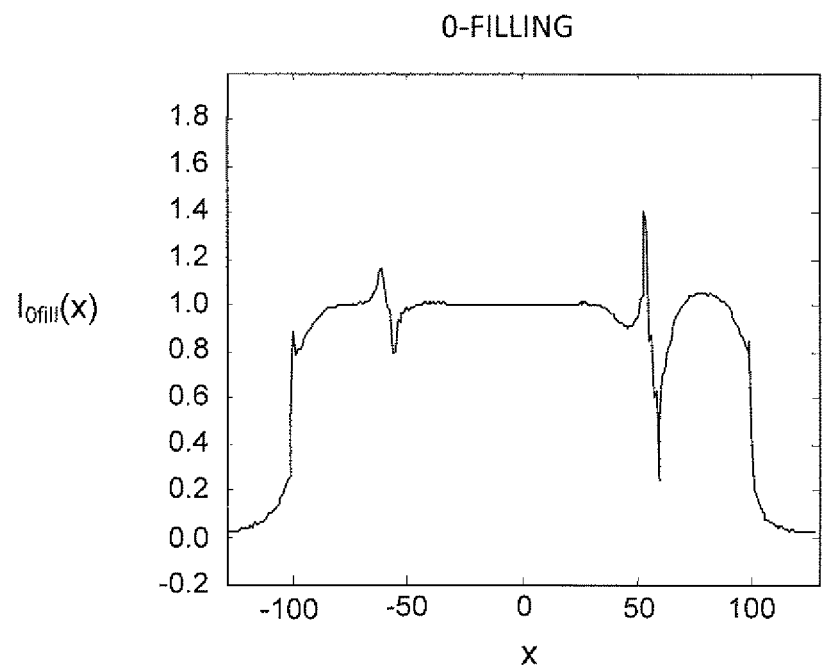
FIG. 11 shows an example of r-space data $I_{0fill}(x)$ generated with 0-filling to asymmetrically sampled k-space data by a one-dimensional simulation.
Figure 12:
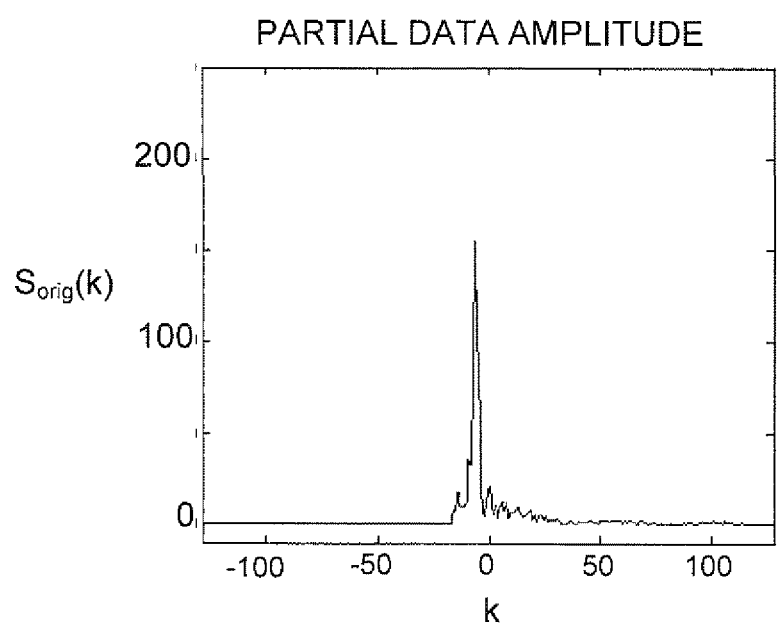
FIG. 12 shows partial original k-space data $S_{orig}(k)$ used for the simulations shown in FIGS. 8 to 12.
Figure 13:
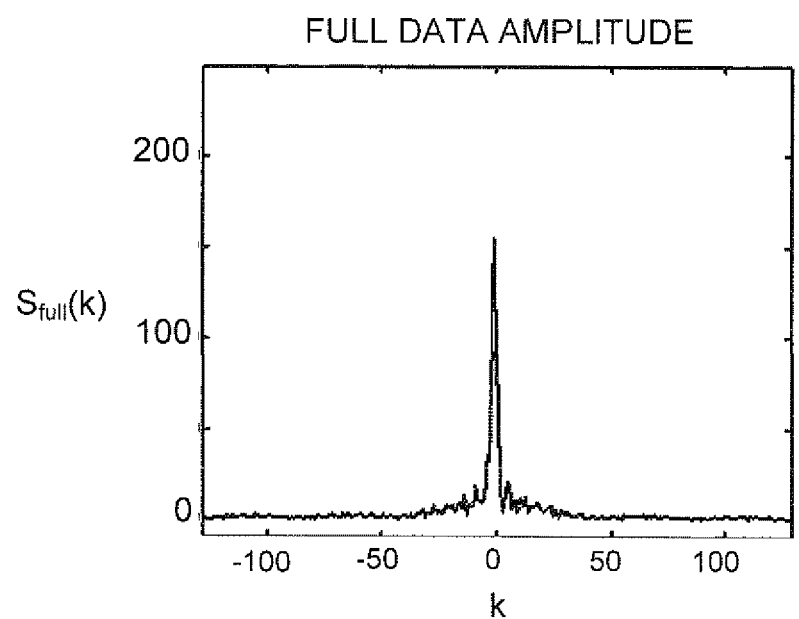
FIG. 13 shows full k-space data $S_{full}(k)$ in the whole frequency range used for generating the partial original k-space data $S_{orig}(k)$ shown in FIG. 12.
Figure 14:
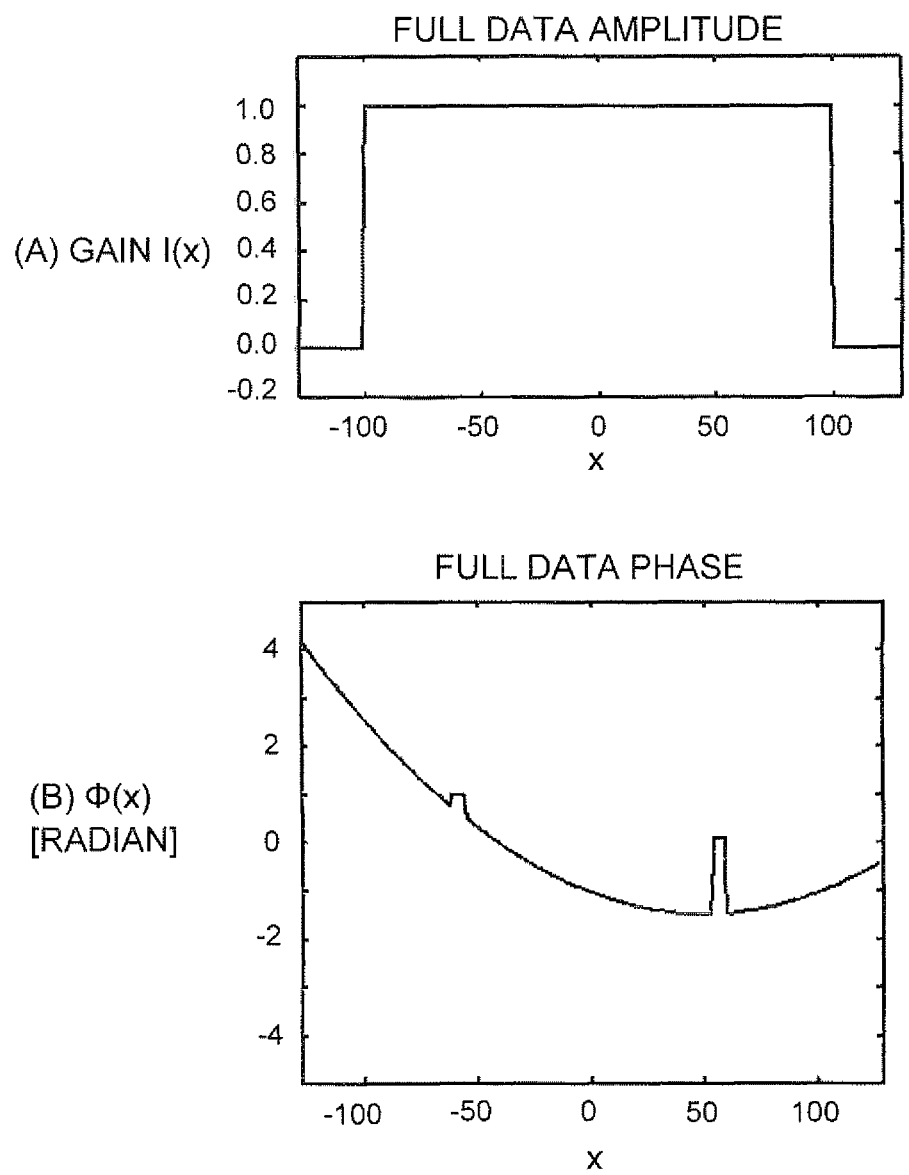
FIG. 14 shows r-space data I(x) and a phase distribution $\Phi(x)$ derived by transforming the full k-space data $S_{full}(k)$ shown in FIG. 13.

FIG. 8 shows an example of r-space data I(x) generated by the first AFI processing in a one-dimensional simulation. FIG. 9 shows an example of r-space data I(x) generated by the second AFI processing in a one-dimensional simulation. FIG. 10 shows an example of r-space data I(x) generated by the third AFI processing in a one-dimensional simulation. FIG. 11 shows an example of r-space data $I_{0fill}(x)$ generated with 0-filling to asymmetrically sampled k-space data by a one-dimensional simulation. FIG. 12 shows partial original k-space data $S_{orig}(k)$ used for the simulations shown in FIGS. 8 to 12. FIG. 13 shows full k-space data $S_{full}(k)$ in the whole frequency range used for generating the partial original k-space data $S_{orig}(k)$ shown in FIG. 12. FIG. 14 shows r-space data I(x) and a phase distribution $\Phi(x)$ derived by transforming the full k-space data $S_{full}(k)$ shown in FIG. 13.

In FIGS. 8 to 11, each abscissa axis denotes one-dimensional pixel position x and each ordinate axis denotes r-space data I(x) on the pixel position x. In addition, in FIGS. 8 to 11, Each (A) shows r-space data $I_0(x)$ without the loop processing, i.e., in case of j=0 and each (B) shows r-space data $I_4(x)$ with 4 repetitions of the loop processing, i.e., in case of j=4.

Meanwhile, in FIG. 12, the abscissa axis denotes position k in k-space and the ordinate axis denotes partial original k-space data $S_{orig}(k)$ on the position k. Each piece of r-space data $I_0(x)$ and $I_4(x)$ respectively shown in FIGS. 8, 9 and 10 has been respectively generated from the partial original k-space data $S_{orig}(k)$ ($-16 \leq k \leq 128$) with setting $K_c=16$ as shown in FIG. 12 by the first, second and third AFI processing respectively shown in FIGS. 5, 6 and 7. As a comparative reference, r-space data $I_{0fill}(x)$ which has been generated by 0-filling shown in FIG. 11 is shown.

Note that, the partial original k-space data $S_{orig}(k)$ shown in FIG. 12 has been derived by shifting data, in an asymmetric sampling region of $-16 \leq k \leq 128$ extracted from the full k-space data $S_{full}(k)$ in the whole frequency region shown in FIG. 13, by five phases. FIG. 14 (A) shows r-space data I(x) obtained by FT of the full k-space data $S_{full}(k)$ in the whole frequency region shown in FIG. 13 and FIG. 14 (B) shows a phase distribution $\Phi(x)$ obtained from the r-space data I(x) shown in FIG. 14 (A).

The results of the simulations shown in FIGS. 8 to 11 teach that the second AFI processing, i.e., the method in which the phase correction processing is performed before the homodyne filter processing using a phase distribution $\Phi_{low}(x)$ in a low frequency region, and the third AFI processing, i.e., the method in which the phase correction processing is performed before the homodyne filter processing using a phase distribution $\Phi_{whole}(x)$ in the whole frequency region make it possible to reduce errors in the phase correction.

The loop processing, for reducing errors in the phase correction, shown in FIGS. 5, 6 and 7 shows a faster convergence in case where errors in the phase correction are less before the loop processing. Therefore, the second AFI processing and the third AFI processing are appropriate in view of speeding up the AFI processing. Especially, adopting the second AFI processing or the third AFI processing, in which the phase correction processing is performed before the homodyne filter processing, is appropriate in case where a phase error is large such as a case where a peak of the partial original k-space data $S_{orig}(k)$ shifts from the center of k-space.

Meanwhile, the third AFI processing, in which the phase distribution $\Phi_{whole}(x)$ in the whole frequency region is used, shows the least errors in the phase correction in case where the loop processing is not performed. Therefore, the third AFI processing is suitable for shortening the data processing period with keeping an image quality.

In addition, it is recognized that perform the loop processing in the third AFI processing can improve errors in the phase correction. Therefore, the third AFI processing with the loop processing is a processing condition suitable for further improving an image quality. However, it has been recognized by the simulations that four and above repetitions of the loop processing does not show a remarkable improvement of phase correction errors though the loop processing can improve phase correction errors each having an order lower than second order.

On the other hand, it is recognized that the second AFI processing, in which a phase distribution $\Phi_{low}(x)$ in a low frequency region is used, cannot improve errors in the phase correction as such even with the loop processing. Therefore, the second AFI processing without the loop processing is preferable not so as to increase the data processing period when a phase distribution $\Phi_{whole}(x)$ in the whole frequency region cannot be obtained.

On the contrary, the first AFI processing, in which the phase correction processing is preformed after the homodyne filter processing, cannot correct a large phase deviation such as a first order of peak shift sufficiently by the phase correction. However, it has been recognized that repetitions of the loop processing can improve errors in the phase correction. Meanwhile, it has been recognized that four and above repetitions of the loop processing does not show a remarkable improvement in the phase correction errors also in the first AFI processing.

Next, an example of determining an appropriate gain of the homodyne filter by a simulation will be described.

The theoretical value of the maximum gain $H_{homo.max}$ of the homodyne filter for an asymmetric sampling region in k-space data lies in the range of $2 \leq H_{homo.max} \leq 4$ on the assumption that errors in the phase correction are negligible after the phase correction. Note that, the maximum gain $H_{homo.max}$ of the homodyne filter for an asymmetric sampling region has been conventionally set to the fixed value of 2.

However, setting the maximum gain $H_{homo.max}$ of the homodyne filter to a value of 2 up to 4 may increase artifacts in case where errors estimated in the phase distribution remain or the estimated errors are emphasized by the phase correction. Therefore, setting the maximum gain $H_{homo.max}$ of the homodyne filter for an asymmetric sampling region to a value less than the theoretical value is sometimes appropriate.

Setting the maximum gain $H_{homo.max}$ of the homodyne filter to 1 ($H_{homo.max}=1$) is equivalent to performing 0-filling. Therefore, setting the maximum gain $H_{homo.max}$ of the homodyne filter to a value more than 1 ($H_{homo.max}>1$) can improve at least a spatial resolution more than 0-filling. Accordingly, setting $1<H_{homo.max}<2$, e.g., setting the maximum gain $H_{homo.max}$ of the homodyne filter to 1.5 ($H_{homo.max}=1.5$), is expected to improve a spatial resolution more than 0-filling without emphasizing errors in the phase correction.

The maximum gain $H_{homo.max}$ of the homodyne filter for an asymmetric sampling region can be set to a value appropriate for each of the first, second and third AFI processing.

In the second and third AFI processing in which the phase correction is performed precedently to the homodyne filter processing, transforming r-space data after the phase correction to k-space data causes leak of signals into the non-sampling part. That is, signal component in the sampling part becomes signal component in the non-sampling part.

Particularly, the imaginary part of signal becomes a value close to zero by the phase correction using a phase distribution in the whole frequency region in the third AFI processing. Therefore, the real part of k-space data becomes approximately symmetric with regard to k=0. For that reason, signal intensity of k-space data in the non-sampling part becomes about ½. Hence, setting the maximum gain $H_{homo.max}$ of the homodyne filter to 4 (=2×2) is reasonable for improving fuzziness in an image due to the signal intensity showing the value of zero in the non-sampling part if phase error is negligible in the third AFI processing.

Also in the second AFI processing, signals leak in the non-sampling part. Therefore, setting the maximum gain $H_{homo.max}$ of the homodyne filter to a value more than 2 is appropriate if phase error is negligible.

As described above, for the first AFI processing, i.e., a case where the phase correction processing is performed after the homodyne filter processing, the maximum gain $H_{homo.max}$ of the homodyne filter is preferable to be set as a value of $1<H_{homo.max}\le2$ or $1<H_{homo.max}<2$ in order to prevent emphasis of errors in the phase correction. On the other hand, for the second and third AFI processing, i.e., cases where the phase correction processing is performed before the homodyne filter processing, the maximum gain $H_{homo.max}$ of the homodyne filter is preferable to be set as a value of $2\le H_{homo.max}\le4$ or $2<H_{homo.max}\le4$ assuming that a phase correction error is not taken into consideration. Thus, a variable setup of the maximum gain $H_{homo.max}$ of the homodyne filter to a value other than 2 can be carried out.

Next, an example of determining the maximum gain $H_{homo.max}$ of the homodyne filter by focusing attention on a degree of phase correction error will be described.

Figure 15:
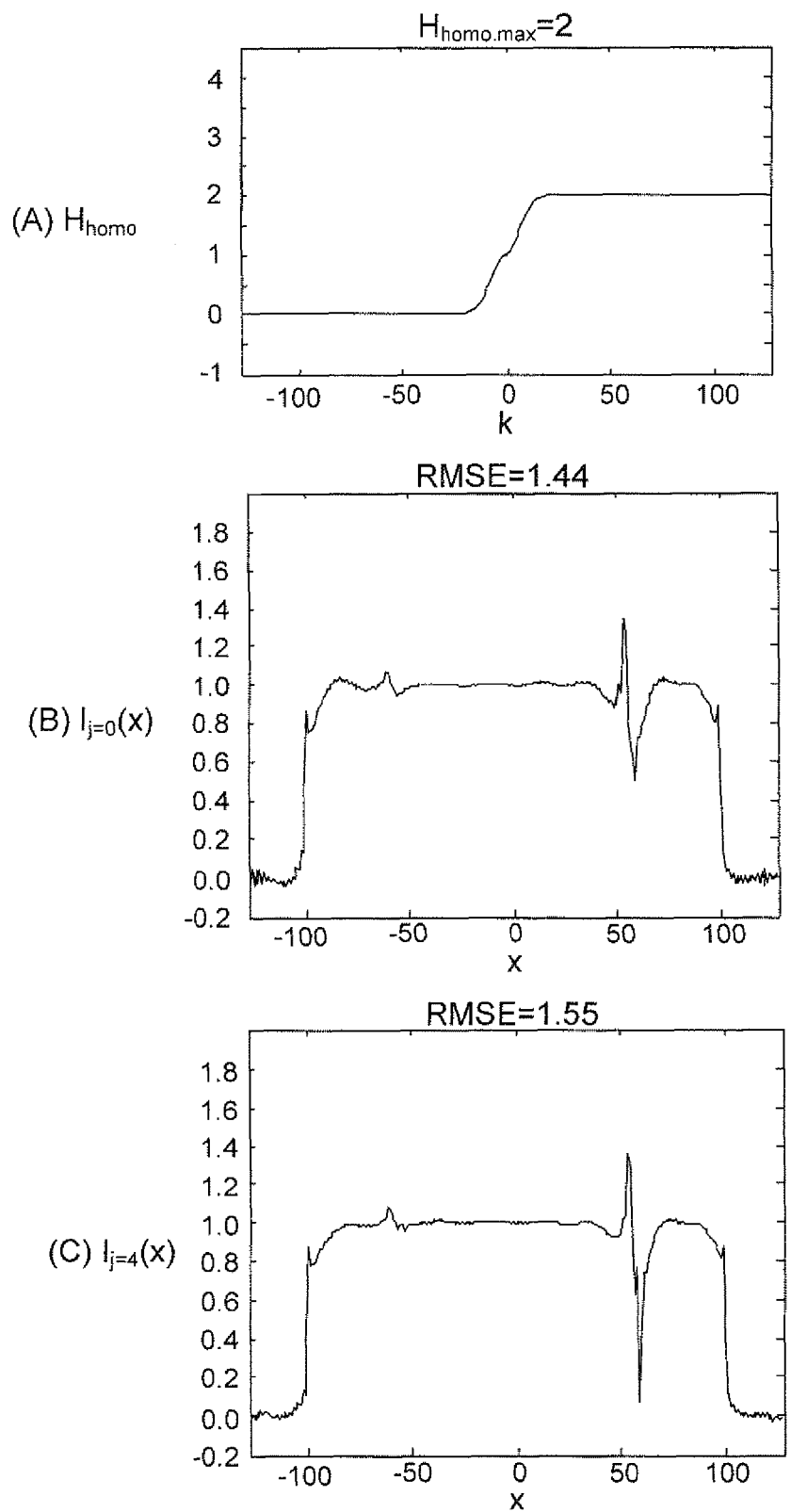
FIG. 15 shows a simulation result in the third AFI processing with setting a gain $H_{homo.max}=2$, corresponding to the asymmetric sampling region, of the homodyne filter.
Figure 16:
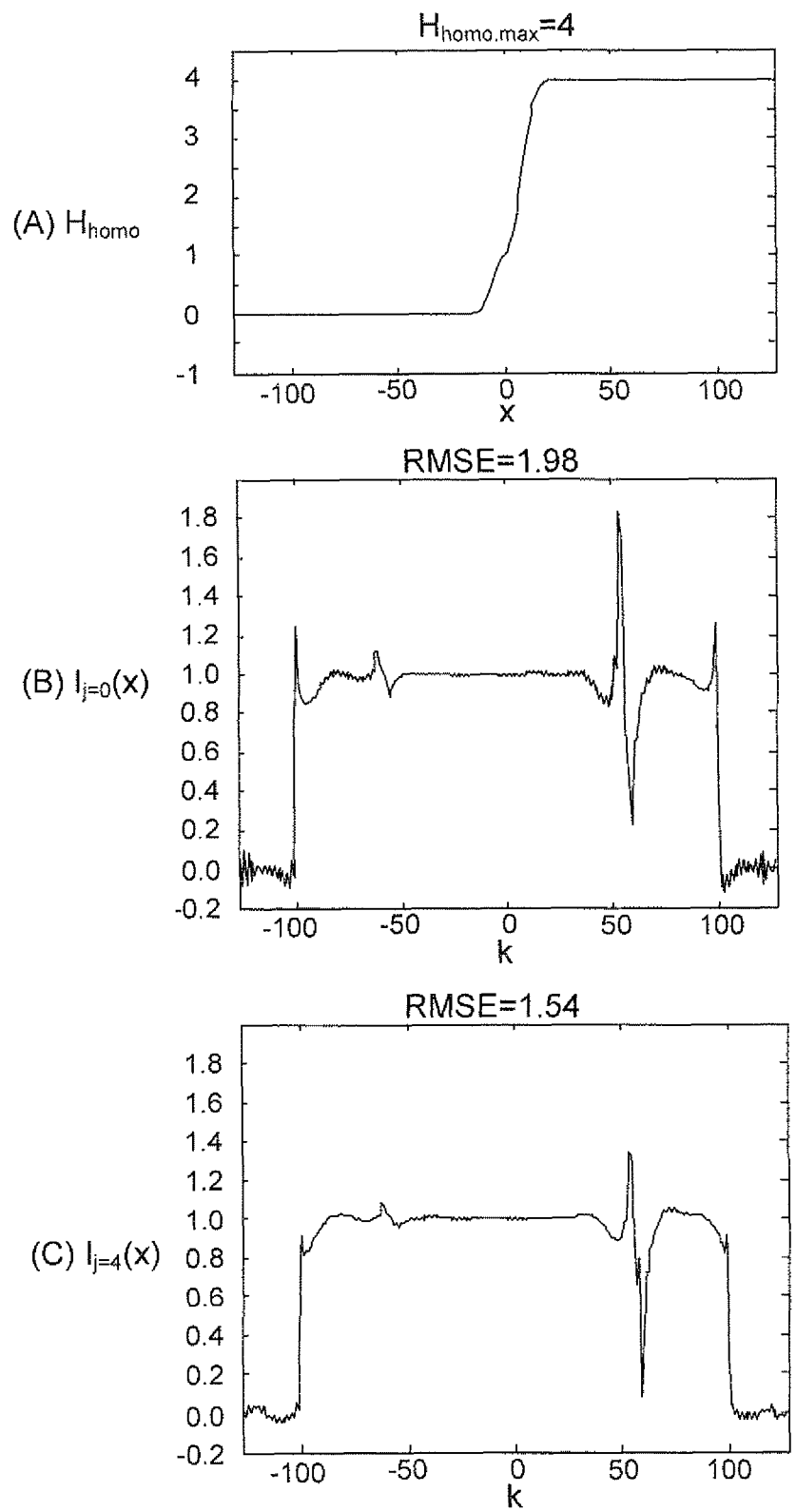
FIG. 16 shows a simulation result in the third AFI processing with setting a gain $H_{homo.max}=4$, corresponding to the asymmetric sampling region, of the homodyne filter.

FIG. 15 shows a simulation result in the third AFI processing with setting a gain $H_{homo.max}=2$, corresponding to the asymmetric sampling region, of the homodyne filter. FIG. 16 shows a simulation result in the third AFI processing with setting a gain $H_{homo.max}=4$, corresponding to the asymmetric sampling region, of the homodyne filter.

FIG. 15 (A) shows a distribution of strength (gain) $H_{homo}$ of the homodyne filter, having the maximum gain $H_{homo.max}=2$ corresponding to the asymmetric sampling region, in the k direction. Performing the third AFI processing with applying the homodyne filter shown in FIG. 15 (A) to k-space data after the phase correction without the loop processing (as j=0) generates the r-space data $I_0(x)$ shown in FIG. 15 (B). Meanwhile, performing the third AFI processing with applying the homodyne filter shown in FIG. 15 (A) and the four repetitions of the loop processing (as j=4) generates the r-space data $I_4(x)$ shown in FIG. 15 (C).

On the other hand, FIG. 16 (A) shows a distribution of strength (gain) $H_{homo}$ of the homodyne filter, having the maximum gain $H_{homo.max}=4$ corresponding to the asymmetric sampling region, in the k direction. Performing the third AFI processing with applying the homodyne filter shown in FIG. 16 (A) to k-space data after the phase correction without the loop processing (as j=0) generates the r-space data $I_0(x)$ shown in FIG. 16 (B). Meanwhile, performing the third AFI processing with applying the homodyne filter shown in FIG. 16 (A) and the four repetitions of the loop processing (as j=4) generates the r-space data $I_4(x)$ shown in FIG. 16 (C).

By FIGS. 15 and 16, it is recognized that signal intensity in the high frequency part in case of setting the maximum gain $H_{homo.max}$ of the homodyne filter to 4 becomes larger than that in case of setting the maximum gain $H_{homo.max}$ of the homodyne filter to 2 when the loop processing is not performed. On the contrary, when the loop processing is performed, pieces of r-space data $I(x)$ having mutually similar distributions of signal intensities are generated whether the maximum gain $H_{homo.max}$ of the homodyne filter is set to 2 or 4.

The reason of this result is considered that a part of k-space data is replaced with the original data after transformation of r-space data to k-space data in the loop processing. That is, pieces of r-space data $I(x)$ having mutually equivalent distributions of signal intensities are generated without depending on the maximum gain $H_{homo.max}$ of the homodyne filter because the imaginary part of signal after the phase correction becomes zero to correct phase correction error by the loop processing.

In addition, RMSE (Root Mean Square Error) of each piece of r-space data $I(x)$, generated by changing the maximum gain $H_{homo.max}$ of the homodyne filter and the number j of repetitions of the loop processing, to full k-space data $S_{full}(k)$ has been calculated. As a result, RMSE=1.44 when $H_{homo.max}=2$ and j=0, RMSE=1.55 when $H_{homo.max}=2$ and j=4, RMSE=1.98 when $H_{homo.max}=4$ and j=0, and RMSE=1.54 when $H_{homo.max}=4$ and j=4. Specifically, setting the maximum gain $H_{homo.max}$ of the homodyne filter corresponding to the asymmetric sampling region to 2 ($H_{homo.max}=2$) makes it possible to reduce the RMSE more satisfactorily when the loop processing is not performed.

Therefore, referring to the simulations shown in FIGS. 15 and 16, setting the maximum gain $H_{homo.max}$ of the homodyne filter corresponding to the asymmetric sampling region to 2 ($H_{homo.max}=2$) is appropriate in view of reducing the RMSE so long as conditions with regard to the spatial resolution and phase correction error are satisfied.

Figure 17:
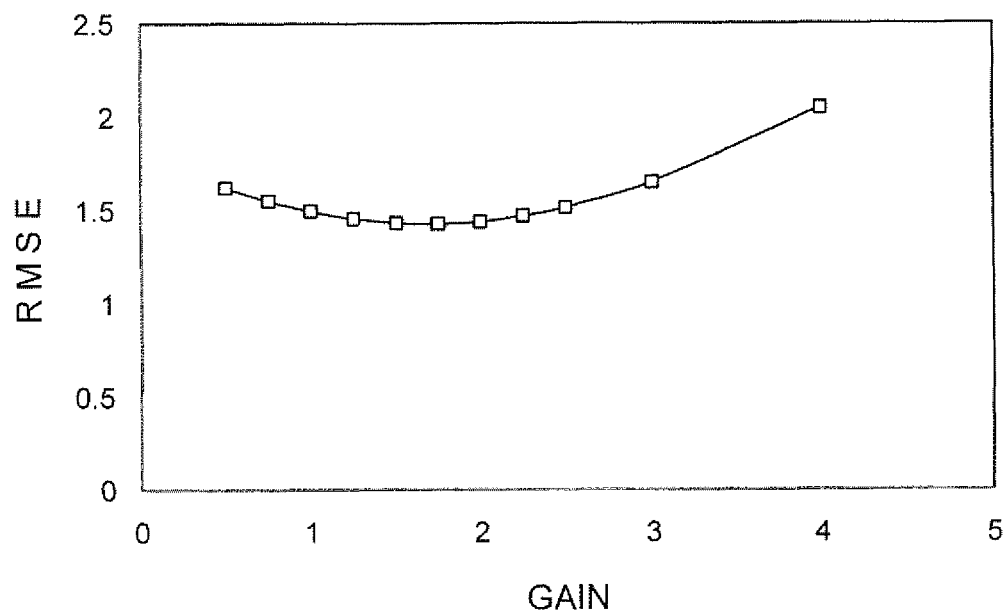
FIG. 17 shows a variation in RMSE in case of changing the maximum gain $H_{homo.max}$, corresponding to the asymmetric sampling region, of the homodyne filter in the third AFI processing.
Figure 18:
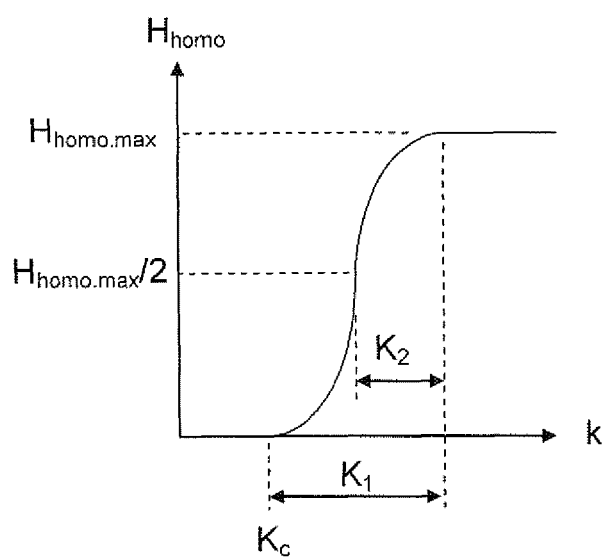
FIG. 18 is a graph for explaining parameters determining a shape of strength distribution of the homodyne filter.

FIG. 17 shows a variation in RMSE in case of changing the maximum gain $H_{homo.max}$, corresponding to the asymmetric sampling region, of the homodyne filter in the third AFI processing. FIG. 18 is a graph for explaining parameters determining a shape of strength distribution of the homodyne filter.

In FIG. 17, the abscissa axis denotes the maximum gain $H_{homo.max}$ of the homodyne filter and the ordinate axis denotes summation of RMSEs for 256 pixels within $-128\le x\le128$. In FIG. 18, the abscissa axis denotes position k in k-space and the ordinate axis denotes strength $H_{homo}$ of the homodyne filter.

In the third AFI processing, the homodyne filter has been applied to k-space data, after the phase correction using a phase distribution $\Phi_{whole}(x)$ in the whole frequency region, with changing the maximum gain $H_{homo.max}$ to 0.5 up to 4.0 by 0.25. Then, the RMSE between the profile of r-space data $I(x)$ within the whole region of $-128\le x\le128$ generated by the third AFI processing of the partial original k-space data $S_{orig}(k)(-K_c=-16\le k\le K_{max}=128)$ of which border $K_c$ of the sampling region is set to 16 ($K_c=16$) and the profile of r-space data $I(x)$ within the whole region of $-128\le x\le128$ corresponding to the full sampling data $S_{full}(k)$ ($-K_{max}=-128\le k\le K_{max}=128$).

In the example shown in FIG. 17, the RMSE becomes the minimum at the maximum gain $H_{homo.max}=1.75$ of the homodyne filter. The theoretical value of the maximum gain $H_{homo.max}$ of the homodyne filter at which the RMSE becomes the minimum is 4. Therefore, the example shown in FIG. 17 shows a case where the maximum gain $H_{homo.max}$ of the homodyne filter at which the RMSE becomes the minimum is much smaller than the theoretical value. The reason of this result is considered that a spatial distribution of phase has much high frequency component.

As described above, in the second and third AFI processing, setting the maximum gain of the homodyne filter to a value within $2=H_{homo.max}\leq 4$ is preferable in view of leakage of signals into the non-sampling part.

Meanwhile, the maximum gain $H_{homo.max}$ of the homodyne filter is sometimes preferable to be set to a value within $1<H_{homo.max}<2$ for minimizing the RMSE when a phase correction error is not negligible due to much high frequency component in a spatial distribution of phase. Therefore, a probable range of the maximum gain of the homodyne filter may be changed between $1<H_{homo.max}\leq 2$ and $2\leq H_{homo.max}\leq 4$ according to a frequency distribution of phase used for the phase correction.

Note that, the parameter $K_1$ which determines the shape $H_{homo}$ of strength distribution of the homodyne filter is set to 16 for calculation of the RMSE ($K_1=16$) in FIG. 17. Specifically, the parameters determining the shape $H_{homo}$ of strength distribution of the homodyne filter include $K_1$ and $K_2$ as well as the border $K_c$ of the sampling region as shown in FIG. 18.

The border $K_c$ of the sampling region is the starting point of rising edge on the strength $H_{homo}$ of the homodyne filter. Further, the strength $H_{homo}$ of the homodyne filter becomes the constant maximum value $H_{homo.max}$ at the position which travels from the border $K_c$ by a distance $K_1$ in k-space. Moreover, a distance between the position in k-space at which the strength $H_{homo}$ of the homodyne filter becomes ½ of the maximum value $H_{homo.max}$ and the position in k-space at which the strength $H_{homo}$ of the homodyne filter becomes the maximum value $H_{homo.max}$ is expressed by $K_2$. Therefore, setting the $K_1$ to a smaller value makes a shape of strength distribution of the filter more rectangular.

In the example shown by FIG. 17, the RMSE has been calculated based on a difference in the whole profile of r-space data I(x). However, the RMSE may be calculated based on a difference in a profile only in a region showing a large phase error.

The optimum value of the maximum gain $H_{homo.max}$ of the homodyne filter corresponding to the asymmetric sampling region depends on data to be a target of the homodyne filter and cannot be calculated without symmetrically sampled k-pace data exactly. Accordingly, the maximum gain $H_{homo.max}$ of the homodyne filter can be determined by various approaches as well as ways based on the type of the AFI processing and/or the RMSE as described above.

For example, pieces of image data corresponding to plural mutually different maximum gains $H_{homo.max}$ of the homodyne filter may be generated by the AFI processing with gradually changing the maximum gain $H_{homo.max}$, similarly to the border $K_c$ of the sampling region, and the generated plural pieces of image data may be displayed on the display unit 34. In this case, inputting information for selecting a frame of image data showing a higher image quality according to the phase distribution from the input device 33 to the AFI processing condition setting unit 42 allows the AFI processing condition setting unit 42 to set the maximum gain $H_{homo.max}$ of the homodyne filter corresponding to the frame of image data showing the higher image quality as an AFI processing condition. Selection of a frame of image data showing a higher image quality may be performed by visual check of a user or by image processing automatically.

Alternatively, the maximum gain $H_{homo.max}$ of the homodyne filter can be also determined experimentally in advance based on other MR data acquired from the same target organ or the same imaging part under data acquisition conditions of which specific conditions are identical to those of MR data acquisition conditions for AFI by using a sequence of which type is same as the sequence used for the AFI, i.e., of which specific conditions for data acquisition are identical to those of the sequence used for the AFI. Herewith, the maximum gain $H_{homo.max}$ of the homodyne filter can be determined appropriately according to imaging conditions influencing the phase distribution. In this case, it is important that an identical degree in data acquisition conditions influencing the phase distribution such as TE is the required ratio. Then, the maximum gain $H_{homo.max}$ of the homodyne filter previously determined can be used as a constant value in a subsequent corresponding AFI As another method, an average of the maximum gain of the homodyne filter within a possible range depending on a type of the AFI processing may be determined as an AFI processing condition to case data processing. For example, the maximum gain $H_{homo.max}$ of the homodyne filter can be fixed to 1.5, which is the intermediate value in the range of $1<H_{homo.max}\leq 2$, for the first AFI processing. Meanwhile, the maximum gain $H_{homo.max}$ of the homodyne filter can be fixed to 3, which is the intermediate value in the range of $2\leq H_{homo.max}\leq 4$, for the second or third AFI processing.

On the other hand, the appropriate maximum gain $H_{homo.max}$ of the homodyne filter can be determined by calculation. Here, two example cases will be described. One example case is that the maximum gain $H_{homo.max}$ of the homodyne filter is calculated by an optimizing calculation minimizing an index value of phase correction error. The other example is that the maximum gain of the homodyne filter is calculated by a calculation using an index value representing a degree of signal leak in the non-sampling part of k-space data due to the phase correction. Both the index value of phase correction error and the index value representing the degree of signal leak in the non-sampling part of k-space data due to the phase correction become values depending on the phase distribution used for the phase correction and imaging conditions influencing the phase distribution.

For example, an index value of phase correction error can be defined with a subtraction value between r-space data $I_{0fill}(x)$ generated by 0-filling of the partial original k-space data $S_{orig}(k)$ and r-space data $I_{AFI}(x)$ generated by the AFI processing. Then, the maximum gain $H_{homo.max}$ of the homodyne fitter can be determined by an optimizing calculation minimizing the index value of phase correction error in a possible range of the maximum gain $H_{homo.max}$ of the homodyne filter, e.g., $1<H_{homo.max}\leq 2$ or $2\leq H_{homo.max}\leq 4$.

Figure 19:
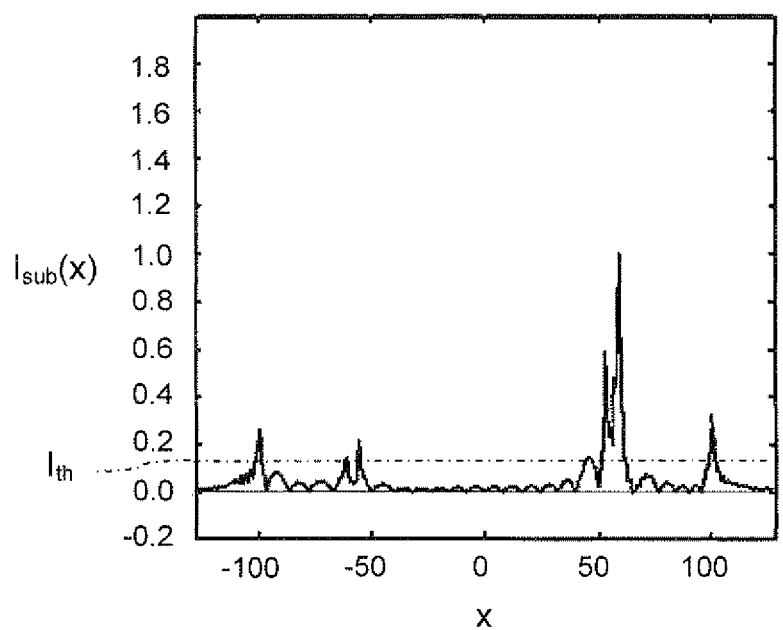
FIG. 19 is a graph for explaining a method of determining the maximum gain $H_{homo.max}$ of the homodyne filter so that an index value of phase correction error based on data generated with 0-filling becomes minimum.

FIG. 19 is a graph for explaining a method of determining the maximum gain $H_{homo.max}$ of the homodyne filter so that an index value of phase correction error based on data generated with 0-filling becomes minimum.

In FIG. 19, the abscissa axis denotes pixel position x and the ordinate axis denotes absolute value $I_{sub}(x)$ of subtraction at pixel position x between r-space data $I_{AFI}(x)$ generated by the AFI processing and r-space data $I_{0fill}(x)$ generated by 0-filling. As shown in FIG. 19, a threshold value $I_{th}$ can be set to the absolute value $I_{sub}(x)$ of subtraction between the AFI r-space data $I_{AFI}(x)$ and the 0-filling r-space data $I_{0fill}(x)$, and a summation of the absolute value $I_{sub}(x)$ beyond the threshold value $I_{th}$ can be used as an index value ErrorSum of the phase correction error.

Specifically, the index value ErrorSum of the phase correction error can be calculated by an algorithm shown by equation (13).

for all pixels (x)

$I_{sub}(x)=|I_{AFI}(x)-I_{0fill}(x)|$ if $I_{sub}(x)>I_{th}$

ErrorSum=ErrorSum+$I_{sub}(x)$ end end (13)

Then, a more appropriate value of the maximum gain $H_{homo.max}$ of the homodyne filter can be obtained by a convergence calculation which changes the maximum gain $H_{homo.max}$ of the homodyne filter within a possible range so that the index value ErrorSum of the phase correction error becomes minimum.

Further, a range showing large difference between the AFI r-space data $I_{AFI}(x)$ and the 0-filling r-space data $I_{0fill}(x)$ can be extracted selectively by threshold processing of the difference between the AFI r-space data $I_{AFI}(x)$ and the 0-filling r-space data $I_{0fill}(x)$ to be used for the calculation of the index value ErrorSum of the phase correction error. Consequently, blur occurring in case of calculating the index value ErrorSum of the phase correction error using difference at all positions between the AFI r-space data $I_{AFI}(x)$ and the 0-filling r-space data $I_{0fill}(x)$ can be prevented Note that, the algorithm shown in FIG. 13) calculates an added value of the absolute value $I_{sub}(x)$ of difference in amplitude between the AFI r-space data $I_{AFI}(x)$ and the 0-filling r-space data $I_{0fill}(x)$ as the index value ErrorSum of the phase correction error. However, the index value ErrorSum of the phase correction error may be defined based on difference in phase between the AFI r-space data $I_{AFI}(x)$ and the 0-filling r-space data $I_{0fill}(x)$. In this case, setting a threshold to the difference in phase can also reduce blur.

As another example, a square mean of the 0-filling r-space data $I_{0fill}(x)$ and the AFI r-space data $I_{AFI}(x)$ of which region corresponding to a range in phase map of the 0-filling r-space data $I_{0fill}(x)$ beyond a predetermined threshold is masked can be defined as the index value ErrorSum of the phase correction error and the optimum maximum gain $H_{homo.max}$ of the homodyne filter can be calculated by a convergence calculation minimizing the index value ErrorSum.

The convergence calculation minimizing the index value ErrorSum of the phase correction error mentioned above may be performed every time when the AFI is performed for improving image quality. However, the convergence calculation leads to increase a data processing period because the convergence calculation includes repetition of the phase correction processing and the homodyne filter processing. For that reason, the maximum gain $H_{homo.max}$ of the homodyne filter which minimizes the index value ErrorSum of the phase correction error may be calculated by a convergence calculation based on data previously acquired from the same target organ or the same imaging part with a same type of sequence as that for the AFI. Herewith, increase of the data processing period can be suppressed.

In case of acquiring multi-slice data in AFI or imaging previously to AFI, results of a convergence calculation are mutually different between slices exactly. Accordingly, an average of the maximum gains $H_{homo.max}$ of the homodyne filter corresponding to the multi slices may be used as the maximum gain $H_{homo.max}$ of the homodyne filter for the AFI processing. Alternatively, the maximum gain $H_{homo.max}$ of the homodyne filter for a single representative slice or the maximum gains $H_{homo.max}$ of the homodyne filter for a few representative slices may be obtained. Herewith, increase of the data processing period can be suppressed.

Note that, in case of performing the loop processing for reducing the phase correction error, the repetition of the loop processing is equivalent to optimizing the maximum gain of the homodyne filter so as to minimize the index value ErrorSum of the phase correction error. Therefore, the process for determining the optimum value of the maximum gain $H_{homo.max}$ of the homodyne filter so that the index value ErrorSum of the phase correction error becomes minimum is not necessary when the loop processing is performed.

However, though the loop processing is performed, a convergence period of the loop processing becomes shorter in case where the maximum gain $H_{homo.max}$ of the homodyne filter is closer to the optimum value. Therefore, optimizing the maximum gain $H_{homo.max}$ of the homodyne filter so that the index value ErrorSum of the phase correction error becomes minimum may be performed for reducing the period of the loop processing.

Next, a method for determining an appropriate value of the maximum gain $H_{homo.max}$ of the homodyne filter using an index representing a degree of signal leak in the non-sampling part of k-space data occurring in the second and the third AFI processing will be described. By this method, an appropriate value of the maximum gain $H_{homo.max}$ of the homodyne filter can be determined more easily than the method using an index value ErrorSum of the phase correction error.

For example, the index representing a degree of signal leak in k-space due to the phase correction can be defined as a symmetric degree in absolute signal value of the k-space data $S_{Pcor}(k)$ after the phase correction.

Figure 20:
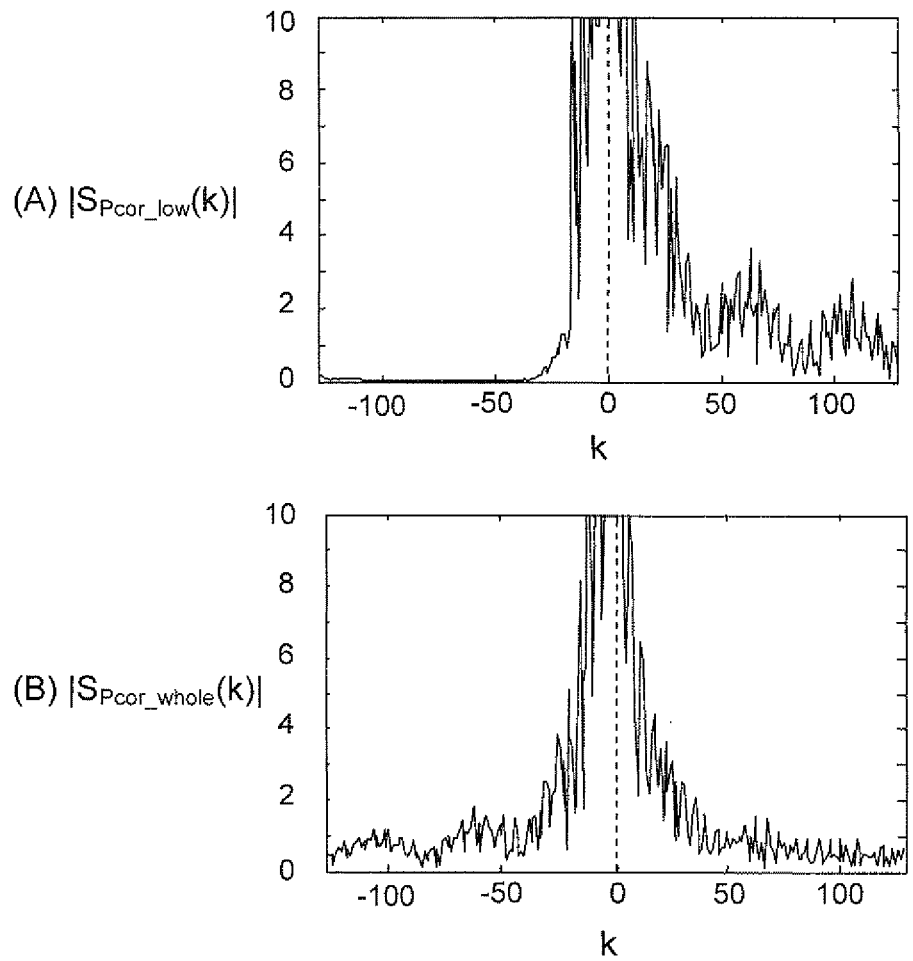
FIG. 20 shows an example of absolute signal values of k-space data $S_{Pcor}(k)$ after the phase correction.
Figure 21:
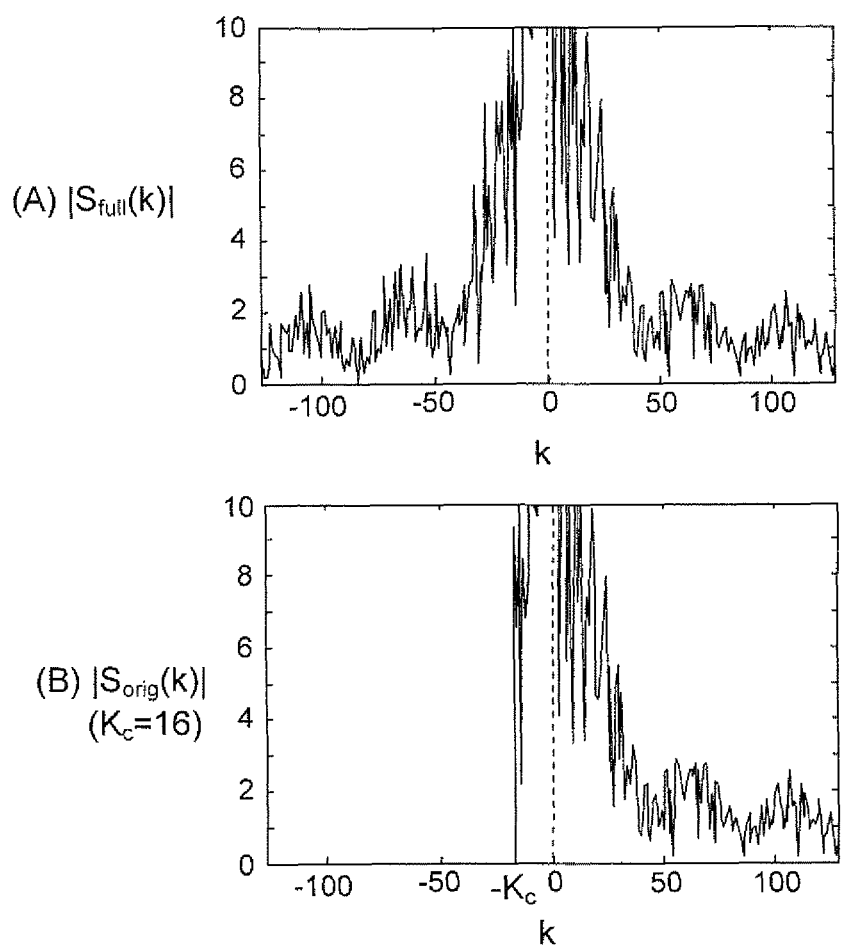
FIG. 21 shows original data used for generating the k-space data $S_{Pcor}(k)$ after the phase correction shown in FIG. 20.

FIG. 20 shows an example of absolute signal values of k-space data $S_{Pcor}(k)$ after the phase correction. FIG. 21 shows original data used for generating the k-space data $S_{Pcor}(k)$ after the phase correction shown in FIG. 20.

In FIGS. 20 and 21, each of the respective abscissa axes denotes position k in a 1D direction of k-space and each of the respective ordinate axes denotes absolute value of signal value of k-space data S(k).

FIG. 20 (A) is an enlarged view showing a profile of absolute signal value $|S_{Pcor\_low}(k)|$ of k-space data $S_{Pcor\_low}(k)$ after the phase correction using phase in a low frequency region in the second AFI processing. Meanwhile, FIG. 20 (B) is an enlarged view showing a profile of absolute signal value $|S_{Pcor\_whole}(k)|$ of k-space data $S_{Pcor\_whole}(k)$ after the phase correction using phase in the whole frequency region in the third AFI processing.

Note that, FIG. 21 (B) shows absolute value $|S_{orig}(k)|$ of partial original k-space data $S_{orig}(k)$ in the range of $-K_c \le k \le K_{max}$ extracted from absolute value $|S_{full}(k)|$ of full sampling k-space data $S_{full}(k)$ shown in FIG. 21 (A) with setting the $K_c=16$. Then, the respective pieces of k-space data $S_{Pcor\_low}(k)$, $S_{Pcor\_whole}(k)$ after the phase corrections shown in (A) and (B) of FIG. 20 are generated by the phase correction of the partial original k-space data $S_{orig}(k)$ shown in FIG. 21 (B).

As shown in FIG. 20 (A), it is recognized that signal component in the sampling region leaks in the non-sampling region of $k<-K_c$ slightly by the phase correction using the phase in the low frequency region. Meanwhile, it is recognized that signal component in the sampling region leaks in the non-sampling region of $k<-K_c$ almost symmetrically with regard to k=0 by the phase correction using the phase in the whole frequency region as shown in FIG. 20 (B).

As shown in (A) and (B) of FIG. 20, the intensity of the signal component in the sampling region becomes lower when the intensity of the signal component leaking in the non-sampling region from the sampling region becomes higher. Accordingly, what is necessary is just to set up the maximum gain $H_{homo.max}$ of the homodyne filter so that the maximum gain $H_{homo.max}$ of the homodyne filter becomes larger within a possible range when the intensity of the signal component leaking in the non-sampling region is higher. That is, an appropriate value of the maximum gain $H_{homo.max}$ of the homodyne filter can be determined depending on the intensity of the signal component leaking in the non-sampling region.

Here, two examples of defining the index representing a degree of the signal leakage into the non-sampling region will be described. The first index SymIndex1 can be defined based on the k-space data $S_{Pcor}(k)$ after the phase correction and the partial original k-space data $S_{orig}(k)$ before the phase correction. Specifically, the first index SymIndex1 can be defined as a ratio of integrated value of the absolute signal intensity $|S_{orig}(k)|$ of the partial original k-space data $S_{orig}(k)$ in the asymmetric part $K_c \le k \le K_{max}$ in the sampling region to integrated value of the absolute signal intensity $|S_{Pcor}(k)|$ of the k-space data $S_{Pcor}(k)$ after the phase correction within the asymmetric part $K_c \le k \le K_{max}$ in the sampling region as shown by equation (14).

$$\text{SymIndex1} = \int_{Kc}^{Kmax} |S_{Pcor}(k)| dk / \int_{Kc}^{Kmax} |S_{orig}(k)| dk \quad (14)$$

When the first index SymIndex1 is defined as shown by equation (14), SymIndex1=1 because the signal intensity within the asymmetric part $K_c \le k \le K_{max}$ in the sampling region does not change before and after the phase correction assuming that no signal leaks in the non-sampling region. On the contrary, when some signal leaks in the non-sampling region symmetrically with regard to k=0, the signal intensity of the k-space data $S_{Pcor}(k)$ after the phase correction within the asymmetric part $K_c \le k \le K_{max}$ in the sampling region becomes ½. Therefore, SymIndex1=0.5.

That is, $0.5 \le \text{SymIndex1} \le 1$. Therefore, the maximum gain $H_{homo.max}$ of the homodyne filter can be determined by equation (15) for example.

$$H_{homo.max} = 2a_1/\text{SymIndex1}$$

$$\therefore 2a_1 \le H_{homo.max} \le 4a_1 \quad (15)$$

In equation (15), $a_1$ is a coefficient having a value of $0 < a_1 \le 1$. The coefficient $a_1$ can be determined with adjustment according to conditions such as a degree of error and the like.

On the other hand, the second index SymIndex2 can be defined based on only the k-space data $S_{Pcor}(k)$ after the phase correction. Specifically, the second index SymIndex2 can be defined as a ratio of an integrated value of the absolute signal intensity $|S_{Pcor}(k)|$ of the k-space data $S_{Pcor}(k)$ after the phase correction in the non-sampling region $-K_{max} \le k \le -K_c$ to that (i.e., an integrated value of the absolute signal intensity $|S_{pcor}(k)|$ of the k-space data $S_{pcor}(k)$ after the phase correction) in the asymmetric part $K_c \le k \le K_{max}$ of the sampling region as shown by equation (16).

$$\text{SymIndex2} = \int_{-Kc}^{-Kmax} |S_{Pcor}(k)| dk / \int_{Kc}^{Kmax} |S_{Pcor}(k)| dk \quad (16)$$

When the second index SymIndex2 is defined as shown by equation (16), SymIndex2=0 assuming that no signal leaks in the non-sampling region. On the contrary, when some signal leaks in the non-sampling region symmetrically with regard to k=0, the k-space data $S_{Pcor}(k)$ after the phase correction becomes symmetric between the asymmetric part $K_c \le k \le K_{max}$ of the sampling region and the non-sampling region $-K_{max} \le k \le -K_c$. Therefore, SymIndex2=1.

That is, $0 \le \text{SymIndex2} \le 1$. Therefore, the maximum gain $H_{homo.max}$ of the homodyne filter can be determined by equation (17).

$$H_{homo.max} = 2a_2(1+\text{SymIndex2})$$

$$\therefore 2a_2 \le H_{homo.max} \le 4a_2 \quad (17)$$

In equation (17), $a_2$ is a coefficient having a value of $0 < a_2 \le 1$. The coefficient $a_2$ can be determined with adjustment according to conditions such as a degree of error and the like.

So far, some cases where the gain $H_{homo.max}$ of the homodyne filter to the asymmetric sampling part is set to a fixed value have been described. However, the gain $H_{homo.max}$ of the homodyne filter to the asymmetric sampling part can be set to a value which is not constant.

Figure 22:
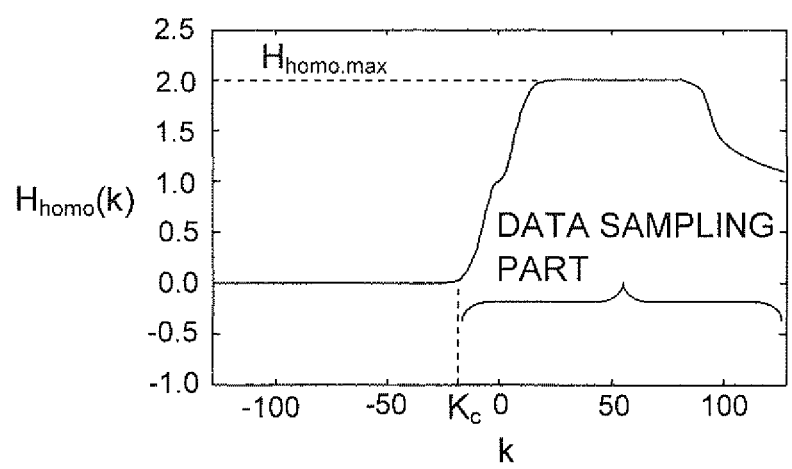
FIG. 22 is a graph showing an example of setting the gain, corresponding to the asymmetric sampling part, of the homodyne filter so as to be gradually attenuated into 1 toward the high frequency part.

FIG. 22 is a graph showing an example of setting the gain, corresponding to the asymmetric sampling part, of the homodyne filter so as to be gradually attenuated into 1 toward the high frequency part.

In FIG. 22, the abscissa axis denotes position k in a 1D direction of k-space and the ordinate axis denotes gain $H_{homo}(k)$ of the homodyne filter at the position k. The k-space data $S_{Pcor}(k)$ after the phase correction has a high possibility that the phase correction error becomes larger in the higher frequency region. Accordingly, giving a characteristic attenuating the gain into 1 more in a higher frequency part to the gain $H_{homo.max}$ of the homodyne filter corresponding to the asymmetric sampling part can relatively reduce signal intensity in a region in which the phase correction error is large.

Note that, FIG. 22 shows an example case where the possible range of the maximum gain $H_{homo.max}(k)$ of the homodyne filter is $1 < H_{homo.max} \le 2$. However, when the possible range of the maximum gain $H_{homo.max}(k)$ of the homodyne filter is $2 \le H_{homo.max} \le 4$, what is necessary is just to set up the gain $H_{homo}(k)$ of the homodyne filter so as to be attenuated into 2 in the range of $2 \le H_{homo.max} \le 4$.

As described above, the shape including the maximum gain $H_{homo.max}(k)$ of the homodyne filter is set in the AFI processing condition setting unit 42. In addition to this, strengths (gains) and shapes of other filters used for the AFI processing are also set in the AFI processing condition setting unit 42.

Figure 23:
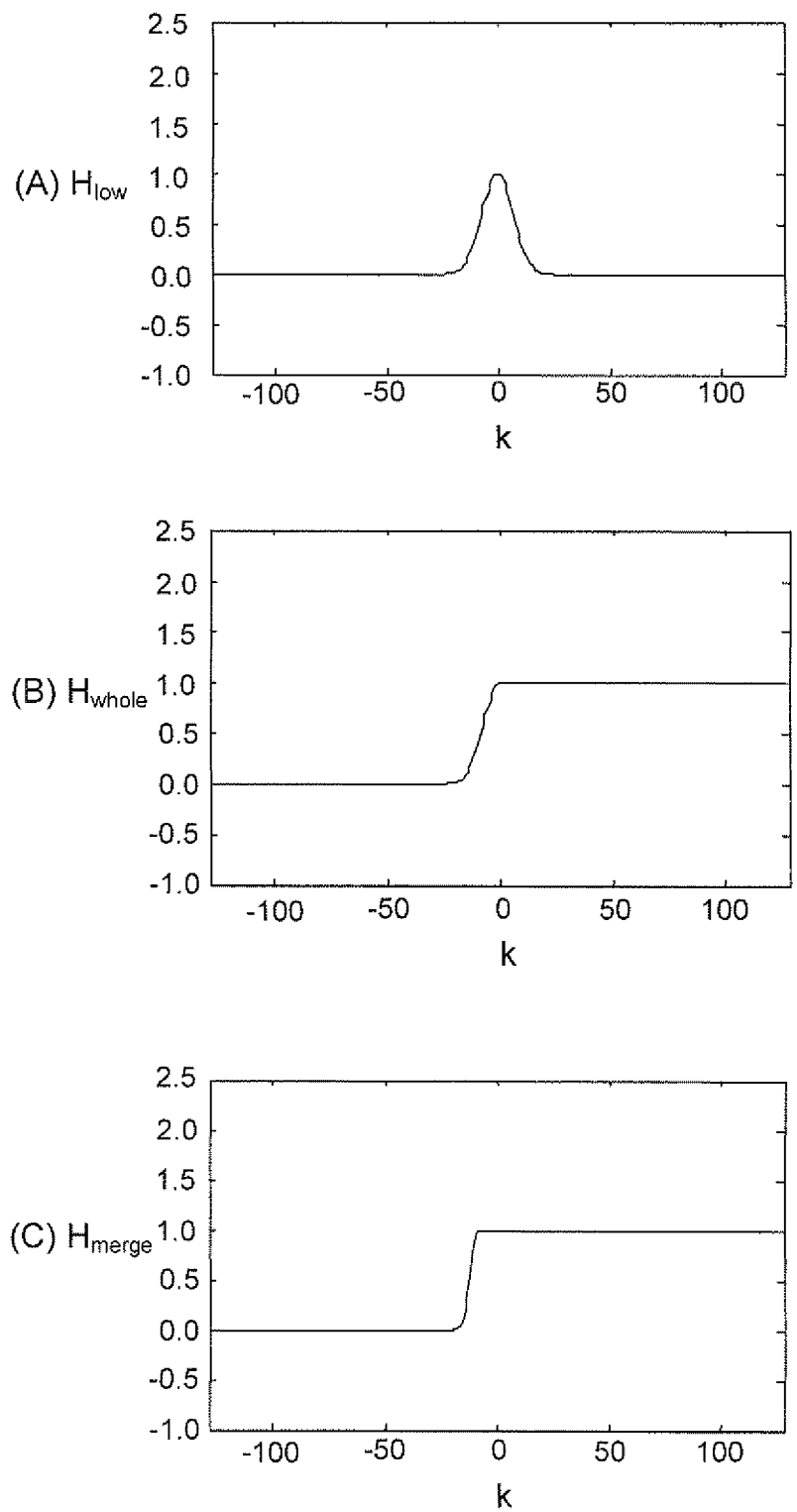
FIG. 23 shows an example of concrete shapes of the filters used for AFI processing.
Figure 24:
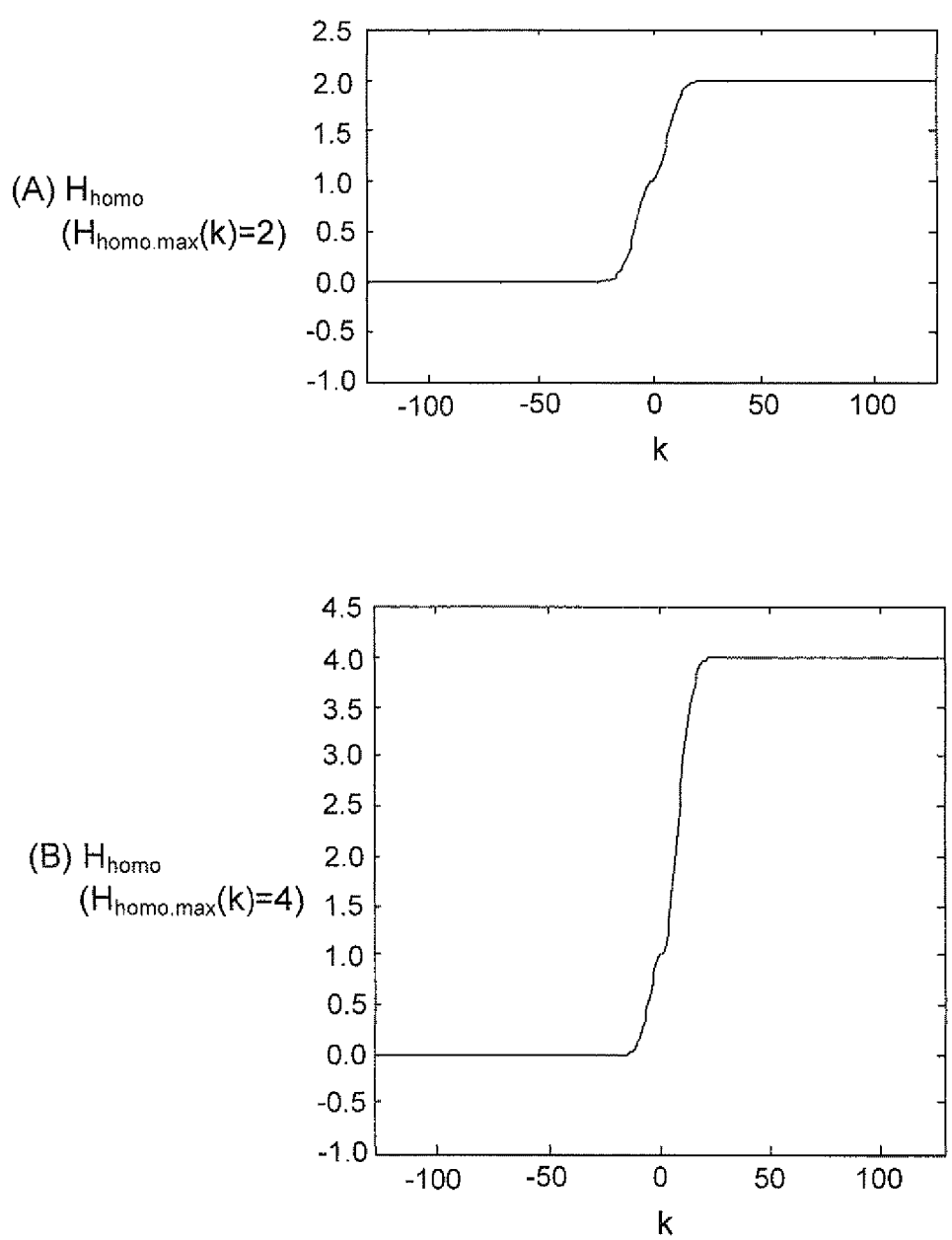
FIG. 24 shows an example of setting the maximum gain $H_{homo.max}(k)$ of the homodyne filter used for AFI processing into a variable value according to a type of the AFI processing.

FIG. 23 shows an example of concrete shapes of the filters used for AFI processing. FIG. 24 shows an example of setting the maximum gain $H_{homo.max}(k)$ of the homodyne filter used for AFI processing into a variable value according to a type of the AFI processing.

In (A), (B) and (C) of FIG. 23 and (A) and (B) of FIG. 24, each abscissa axis denotes position k in a 1D direction of k-space.

FIG. 23 (A) shows an example of shape of the LPF $H_{low}(k)$ for extracting k-space data $S_{low}(k)$ ($-K_c \le k \le K_c$) in the symmetric low frequency part from the asymmetrically sampled partial original k-space data $S_{orig}(k)$. FIG. 23 (B) shows an example of shape of the filter $H_{whole}(k)$ for extracting the entire data in the whole frequency region from the partial original k-space data $S_{orig}(k)$. FIG. 23 (C) shows an example of shape of the data extraction filter $H_{merge}(k)$ for extracting the range of $-K_c \le k \le K_{max}$ from the partial original k-space data $S_{orig}(k)$ for the compound processing in the loop processing.

As shown by equations (18-1), (18-2), (18-3) and (18-4), the LPF $H_{low}(k)$, the data extraction filter $H_{homo.max}(k)$ for the whole frequency region, the data extraction filter $H_{merge}(k)$ for the compound processing and the homodyne filter $H_{homo}(k)$ can be calculated respectively.

$$H_{low}(k)=1 : |k| \leq K_c - K_1$$

$$= exp[(-\ln 2)\{(k-(K_c-K_1))/K_2\}^2] : K_c-K_1 < |k| \leq K_{max} \quad (18\text{-}1)$$

$$H_{whole}(k)=H_{low}(k) : k \leq 0$$

$$=1 : 0 < k \leq K_{max} \quad (18\text{-}2)$$

$$H_{merge}(k)=H_{low}(k) : k \leq 0$$

$$=1 : 0 < k \leq K_{max} \quad (18\text{-}3)$$

$$H_{homo}(k)=H_{low}(k) : k \leq 0$$

$$=H_{homo.max}-(H_{homo.max}-1)H_{low}(k) : 0 < k \leq K_{max} \quad (18\text{-}4)$$

Herewith, the LPF $H_{low}(k)$, the data extraction filter $H_{whole}(k)$ for the whole frequency region and the data extraction filter $H_{merge}(k)$ for the compound processing having shapes as shown in FIG. 23 (A), (B) and (C) respectively are generated. Note that, a Gauss function is used for smoothly changing the transition part of the gain.

In equation (18-4), the maximum gain $H_{homo.max}(k)$ of the homodyne filter can be set as a variable value depending on a type of the AFI processing. For example, in case of the first or second AFI processing which performs the phase correction using the phase distribution $\Phi_{low}(x)$ in the low frequency region, the maximum gain $H_{homo.max}(k)$ of the homodyne filter is set to 2, i.e, $H_{homo.max}(k)=2$, in consideration of the phase correction error. Meanwhile, in case of the third. AFI processing which performs the phase correction using the phase distribution $\Phi_{whole}(x)$ in the whole frequency region, the maximum gain $H_{homo.max}(k)$ of the homodyne filter is set to 4, i.e, $H_{homo.max}(k)=4$.

FIG. 24 (A) shows a shape $H_{homo}(k)$ of the homodyne filter of which the maximum gain $H_{homo.max}(k)=2$ for the first and second AFI processing. Meanwhile, FIG. 24 (B) shows a shape $H_{homo}(k)$ of the homodyne filter of which the maximum gain $H_{homo.max}(k)=4$ for the third AFI processing.

Equations (18-1), (18-2), (18-3) and (18-4) and FIGS. 23 and 24 show an example case of setting the non-sampling region in the negative region of k-space. When the non-sampling region is set in the positive region of k-space, the value of filter strength is inverted between the negative side and positive side of k-space. That is, the left side and the right side are mutually inverted in FIGS. 23 and 24.

Note that, the above mentioned description has shown an example of performing the phase correction of the r-space data $I_{homo}(x)$ or $I_{whole}(x)$ after the filter processing by the homodyne filter $H_{homo}(k)$ or the data extraction filter $H_{whole}(k)$ for the whole frequency region in the AlI processing. However, data processing conditions may be determined so that the zero order phase correction and first order phase correction are performed in k-space as a pre-processing of the AFI processing. That is, at least one of zero order and first order of the phase corrections may be performed to MR data in k-space prior to the homodyne filter processing and the phase correction performed after the homodyne filter processing.

The first order of phase correction to k-space data $S(k)$ corresponds to a position shift for matching a position in k-space of absolute value $|S_{peak}(k)|$ of echo peak of the k-space data $S(k)$ with the center of k-space. Therefore, performing the zero and first order phase corrections or at least the zero order phase correction as a pre-processing of the AFI processing leads to reduce the phase correction error in the AFI processing.

Especially, in case of the first AFI processing which performs the phase correction processing after the homodyne filter processing, the phase correction error occurs due to a possibly large phase error of the asymmetric partial original k-space data $S_{orig}(k)$ by the AFI processing. For that reason, it is preferable to perform a low order of phase correction as a pre-processing of the AFI processing in case of the first AFI processing.

Further, as shown by equation (19-1), r-space data $I_w(x)$ derived by a weighted addition using a weight coefficient w of the AFI r-space data $I_{AFI}(x)$ generated by the AFI processing and the 0-filling r-space data $I_{0fill}(x)$ generated by 0-filling may be used as diagnosis image data. In this case, the weight coefficient w can be set to a difference between the AFI r-space data $I_{AFI}(x)$ and the 0-filling r-space data $I_{0fill}(x)$ as shown by equation (19-2) as an easy example.

$$I_w(x)=w*I_{0fill}(x)+(1-w)*I_{AFI}(x) \quad (19\text{-}1)$$

$$w=|I_{0fill}(x)-I_{AFI}(x)| \quad (19\text{-}2)$$

Whether the zero and first order phase corrections are performed as a pre-processing of the AFI processing or not and whether the weighted addition shown by equations (19-1) and (19-2) is performed or not mentioned above can be also set as data processing conditions in the AFI processing condition setting unit 42.

Then, the operation and action of the magnetic resonance imaging apparatus 20 will be described.

Figure 25:
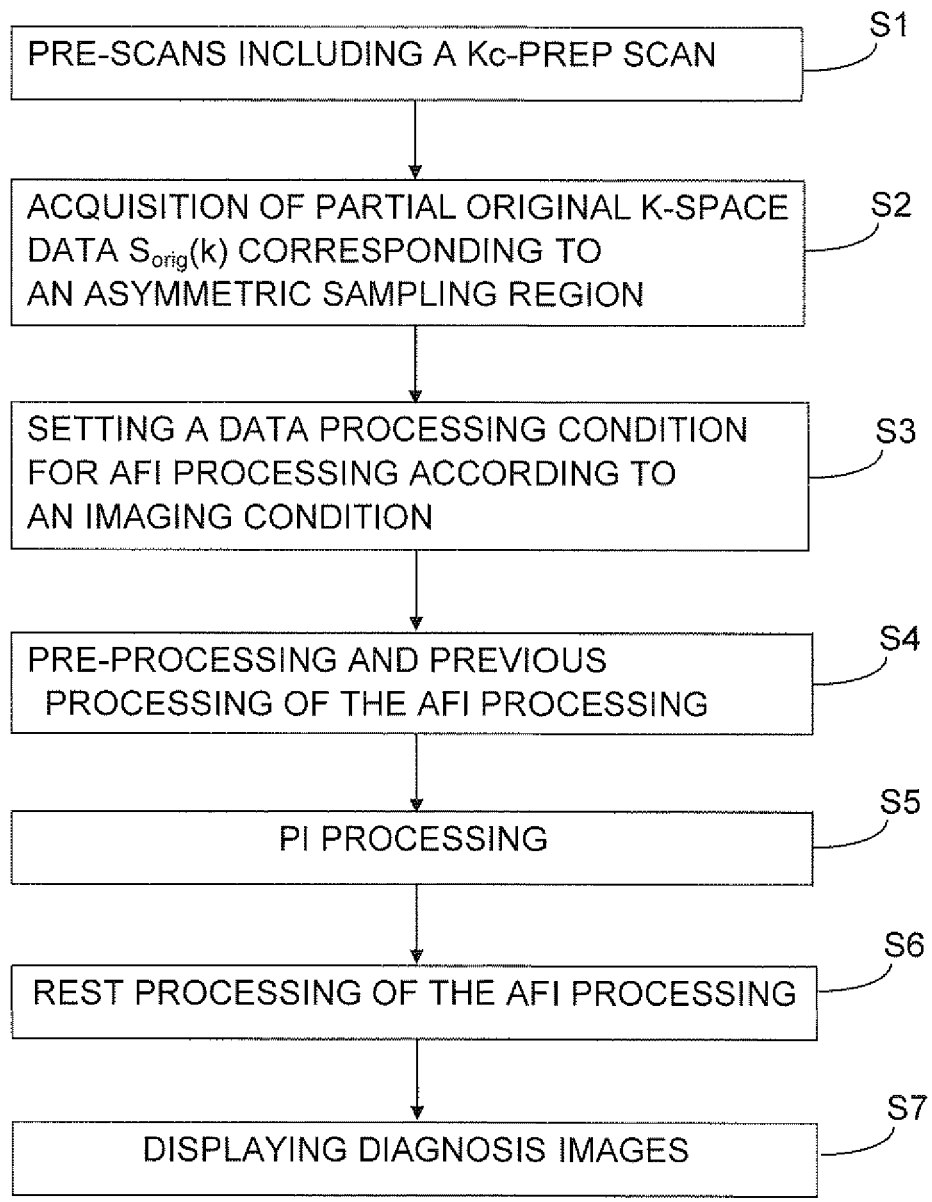
FIG. 25 is a flowchart showing a flow for acquiring diagnostic images by AFI and PI with the magnetic resonance imaging apparatus shown in FIG. 1.

FIG. 25 is a flowchart showing a flow for acquiring diagnostic images by AFI and PI with the magnetic resonance imaging apparatus 20 shown in FIG. 1. Here, the explanation will be given in a case of determining the border $K_C$ of the asymmetric sampling region by a pre-scan.

First, in the step S1, pre-scans including a Kc-PREP scan for determining the border $K_c$ of the data sampling region in AFI are performed prior to an imaging scan. The pre-scans include a pre-scan for shimming and a pre-scan for measuring sensitivity maps of coil elements 24c for PI as well as the Kc-PREP scan.

Specifically, the imaging condition setting unit 40 sets imaging conditions for the pre-scans including the Kc-PREP scan and outputs the set imaging conditions to the sequence controller 31. Herewith, necessary MR data is acquired in a flow similar to that in the imaging scan mentioned below. In addition, a phase distribution in a large frequency region may be obtained for the phase correction in the AFI processing from data acquired by the pre-scan for shimming or the pre-scan for measuring the sensitivity maps of the coil elements 24c.

From MR data acquired by the Kc-PREP scan, pieces of image data are generated by the AFI processing as shown in FIG. 4 (B). Therefore, obtaining the phase distribution by a pre-scan such as the per-scan for shimming prior to the Kc-PREP scan makes it possible to use the phase distribution for the phase correction to the data acquired by the Kc-PREP scan. Then, the border $K_c$ of the data sampling region for the imaging scan can be determined by selecting a piece of image data showing a satisfactory image quality from the pieces of image data acquired by the Kc-PREP scan.

Next, in the step S2, acquisition of MR data corresponding to the data sampling region $-K_c \leq k \leq K_{max}$ in k-space is performed. Specifically, the imaging condition setting unit 40 sets imaging conditions including a desired pulse sequence for acquiring the MR data from the asymmetric data sampling region $-K_c \leq k \leq K_{max}$. Setting the imaging conditions can be performed by selecting a desired imaging protocol from plural alternatives of the imaging protocol displayed on the display unit 34 with operation of the input device 33.

Next, the imaging condition setting unit 40 outputs the imaging conditions including the pulse sequence to the sequence controller 31. Then, the elements of the magnetic resonance imaging apparatus 20 for performing a scan such as the sequence controller 31 and the magnet 21 acquire imaging data corresponding to the asymmetric sampling region $-K_c \leq k \leq K_{max}$ of k-space from the object P according to the set imaging conditions.

For that purpose, the object P is set to the bed 37 previously, and a static magnetic field is generated at an imaging area of the magnet 21 (a superconducting magnet) for static magnetic field excited by the static-magnetic-field power supply 26. Further, the shim-coil power supply 28 supplies necessary current, based on the data acquired by the pre-scan for shimming, to the shim coil 22, thereby uniformizing the static magnetic field generated at the imaging area.

Then, the sequence controller 31 drives the gradient power supply 27, the transmitter 29, and the receiver 30 in accordance with the pulse sequence received from the imaging condition setting unit 40, thereby generating a gradient magnetic field at the imaging area having the set object P, and further generating RF signals from the RF coil 24.

Consequently, the RF coil 24 receives NMR signals generated due to nuclear magnetic resonance in the object P. Then, the receiver 30 receives the NMR signals from the RF coil 24 and generates raw data which is digital data of NMR signals. The receiver 30 supplies the generated raw data to the sequence controller 31. The sequence controller 31 supplies the raw data to the data processing unit 41. The data processing unit 41 arranges the raw data in k-space formed in the k-space database 43 as the partial original k-space data $S_{orig}(k)$ in the asymmetric sampling region 5

On the other hand, in the step S3, the AFI processing condition setting unit 42 sets data processing conditions for the AFI processing such as an appropriate type of the AFI processing according to the imaging conditions, the number j of repetitions of the loop processing for reducing the phase correction error and a strength and a shape of the homodyne filter. Specifically, matters including whether the phase correction processing is performed before or after the homodyne filter processing, whether a phase distribution $\Phi_{whole}(x)$ in the whole frequency region or a phase distribution $\Phi_{low}(x)$ in a low frequency region is used for the phase correction and whether the phase distribution $\Phi(x)$ for the phase correction is estimated from the only k-space data self to be corrected, only other data, or both the self data and the other data, are determined.

For example, the AFI processing condition setting unit 42 can acquire the information for selecting the imaging protocol from the imaging condition setting unit 40 and read the AFI processing conditions previously related with the selected imaging protocol from the AFI condition database 46 to set the AFI processing conditions. In addition, the AFI processing condition setting unit 42 calculates the maximum gain $H_{homo.max}(k)$ of the homodyne filter corresponding to the asymmetric sampling part when the maximum gain $H_{homo.max}(k)$ is obtained by calculation such as a convergence calculation based on the partial original k-space data $S_{orig}(k)$.

Next, the AFI processing condition setting unit 42 also determines an order of various processing consisting of the AFI processing, such as the phase correction and filter processing, and PI processing subsequently to setting the type of the AFI processing. For example, the order in data processing is determined so that the PI unfolding processing and the compound processing of image data are performed after the former processing out of the AFI processing, such as the homodyne filter processing which is preferable to be performed before the compound processing of pieces of image data corresponding to the plural coil elements 24c, and the remaining latter processing out of the AFI processing, such as the loop processing, is performed after the compound processing.

In addition, the zero and first orders of phase correction processing as pre-processing of the AFI processing is set as a data processing condition according to the imaging conditions by the AFI processing condition setting unit 42, as needed.

Then, the AFI processing condition setting unit 42 gives the AFI processing conditions including information with regard to pre-processing and the order of data processing to the AFI processing part 41B.

Next, in the step S4, the AFI processing part 41B performs the pre-processing and the former processing of the AFI processing according to the AFI processing conditions. The data after the processing is given from the AFI processing part 41B to the PI processing part 41A.

Next, in the step S5, the PI processing part 41A performs the PT unfolding processing and the compound processing of pieces of image data. The data after the processing is given from the PI processing part 41A to the AFI processing part 41B.

Next, in the step S6, the AFI processing part 41B performs the latter processing of the AFI processing such as the loop processing according to the AFI processing conditions. Consequently, diagnosis image data is generated with an image quality equivalent to that of image data generated by image reconstruction processing of symmetrically sampled k-space data.

Next, in the step S7, the data processing unit 41 displays the image data for diagnosis, generated by the PI processing and the AFI processing, on the display unit 34. As a result, a user can observe a diagnosis image, having an improved image quality, which has been subjected to the AFI processing under appropriate conditions according to the imaging conditions.

That is, the magnetic resonance imaging apparatus 20 as described above is an apparatus in which a variable setup of data processing conditions for AFI can be carried out appropriately according to at least one of imaging conditions and a phase distribution.

Therefore, the magnetic resonance imaging apparatus 20 can improve accuracy of image in AFI more than a conventional apparatus. That is, an image close to one generated from MR data symmetrically sampled in k-space can be obtained.

In addition, performing the phase correction processing before the homodyne filter processing make it possible to speed up the convergence in the loop processing for reducing error. Consequently, it becomes possible to suppress increase of the data processing period necessary for improving image accuracy to the minimum extent.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
an imaging unit configured to acquire magnetic resonance data corresponding to a sampling region asymmetric in a wave number direction in k-space from an object to generate image data based on the magnetic resonance data by data processing including phase correction and filter processing for obtaining a complex conjugate; and
a data processing condition setting unit configured to set a condition for the data processing according to an imaging condition influencing a phase distribution used for the phase correction or the phase distribution.

2. A magnetic resonance imaging apparatus of claim 1,
wherein said data processing condition setting unit is configured to set at least one of a border of the sampling region, a maximum gain of the filter processing, a shape of a filter used for the filter processing, a repetition number of loop processing for reducing error, whether the phase correction is performed before or after the filter processing, whether a phase distribution in a frequency region corresponding to a data processing range or a phase distribution in a frequency region corresponding to a symmetric part out of the sampling region is used for the phase correction and whether a phase distribution used for the phase correction is obtained from only the magnetic resonance data, only other magnetic resonance data or both the magnetic resonance data and the other magnetic resonance data,
the loop processing being a convergence calculation which repeats processing for obtaining a real part of real space data after the phase correction and the filter processing, processing for returning a phase of the real part so as to be a phase before the phase correction, processing for replacing a part of k-space data obtained by transforming real space data after the processing for returning the phase with the magnetic resonance data and processing for transforming k-space data after the replacement into real space data to perform the phase correction, the convergence calculation being for converging an imaginary part of the real part data to be a target of the processing for obtaining the real part into zero.

3. A magnetic resonance imaging apparatus of claim 1,
wherein said data processing condition setting unit is configured to be able to perform a variable set up of a maximum gain of the filter processing into a value other than 2.

4. A magnetic resonance imaging apparatus of claim 3,
wherein said data processing condition setting unit is configured to set to use a phase distribution in a frequency region corresponding to a data processing range for the phase correction and set the maximum gain of the filter processing into a value not lower than 2 and not more than 4.

5. A magnetic resonance imaging apparatus of claim 3,
wherein said data processing condition setting unit is configured to set to use a phase distribution in a frequency region corresponding to a symmetric part out of the sampling region for the phase correction and set the maximum gain of the filter processing into a value not lower than 1 and not more than 2.

6. A magnetic resonance imaging apparatus of claim 3,
wherein said data processing condition setting unit is configured to set the maximum gain of the filter processing into 1.5 or 3.

7. A magnetic resonance imaging apparatus of claim 3,
wherein said data processing condition setting unit is configured to set a possible range of the maximum gain of the filter processing to a range not lower than 1 and not more than 2 or a range not lower than 2 and not more than 4 according to the phase distribution.

8. A magnetic resonance imaging apparatus of claim 3,
wherein said data processing condition setting unit is configured to set the maximum gain of the filter processing by an optimization calculation for minimizing an index representing a degree of phase correction error within a possible range of the maximum gain of the filter processing.

9. A magnetic resonance imaging apparatus of claim 3,
wherein said data processing condition setting unit is configured to set the maximum gain of the filter processing according to an index representing a degree of signal leak into a part in which the magnetic resonance data is not be sampled.

10. A magnetic resonance imaging apparatus of claim 3,
wherein said data processing condition setting unit is configured to set the maximum gain of the filter processing based on other magnetic resonance data acquired from a same target organ or a same imaging part under data acquisition conditions of which a predetermined condition is identical to that of acquisition conditions for the magnetic resonance data.

11. A magnetic resonance imaging apparatus of claim 1,
wherein said data processing condition setting unit is configured to set a characteristic of a gain of the filter processing to a characteristic attenuated more in a higher frequency region according to the phase distribution.

12. A magnetic resonance imaging apparatus of claim 1,
wherein said imaging unit is configured to perform the phase correction using a phase distribution obtained from magnetic resonance data other than the magnetic resonance data for generating the image data, the other magnetic resonance data being acquired in a frequency region larger than that of the magnetic resonance data for generating the image data.

13. A magnetic resonance imaging apparatus of claim 12,
wherein said imaging unit is configured to perform the phase correction using a phase distribution obtained from magnetic resonance data acquired by a pre-scan for measuring a magnetic field map for shimming of a static magnetic field or a pre-scan for measuring a sensitivity distribution of plural coil elements.

14. A magnetic resonance imaging apparatus of claim 1,
wherein said data processing condition setting unit is configured to set the condition for the data processing so as to perform loop processing and perform the phase correction before the filter processing,
the loop processing including a convergence calculation which repeats processing for obtaining a real part of real space data after the phase correction and the filter processing, processing for returning a phase of the real part so as to be a phase before the phase correction, processing for replacing a part of k-space data obtained by transforming real space data after the processing for returning the phase with the magnetic resonance data and processing for transforming k-space data after the replacement into real space data to perform the phase correction, the convergence calculation being for converging an imaginary part of the real part data to be a target of the processing for obtaining the real part into zero.

15. A magnetic resonance imaging apparatus of claim 1,
wherein said imaging unit is configured to generate pieces of image data corresponding to coil elements by acquiring pieces of magnetic resonance data with the coil elements and perform compound processing of the pieces of the image data previously to loop processing including a convergence calculation which repeats processing for obtaining a real part of real space data after the phase correction and the filter processing, processing for returning a phase of the real part so as to be a phase before the phase correction, processing for replacing a part of k-space data obtained by transforming real space data after the processing for returning the phase with the magnetic resonance data and processing for transforming k-space data after the replacement into real space data to perform the phase correction, the convergence calculation being for converging an imaginary part of the real pan data to be a target of the processing for obtaining the real part into zero.

16. A magnetic resonance imaging apparatus of claim 1, further comprising:
a pre-scan unit configured to acquire pieces of magnetic resonance data with changing a border of the sampling region to generate pieces of image data corresponding to mutually different borders of the sampling region
wherein said data processing condition setting unit is configured to set the border of the sampling region based on information for selecting a piece of image data from the pieces of the image data as the condition for the data processing.

17. A magnetic resonance imaging apparatus of claim 1, further comprising:
a storage unit configured to store data processing conditions corresponding to imaging conditions,
wherein said data processing condition setting unit is configured to acquire a data processing condition corresponding to an imaging condition influencing the phase distribution from the storage unit.

18. A magnetic resonance imaging apparatus of claim 1,
wherein said imaging unit is configured to perform at least one of a zero order of a phase correction and a first order of a phase correction to the magnetic resonance data in k-space previously to the filter processing and the phase correction performed after the filter processing.

19. A magnetic resonance imaging method comprising:
acquiring magnetic resonance data corresponding to a sampling region asymmetric in a wave number direction in k-space from an object to generate image data based on the magnetic resonance data by data processing including phase correction and filter processing for obtaining a complex conjugate; and
setting a condition for the data processing according to an imaging condition influencing a phase distribution used for the phase correction or the phase distribution.

* * * * *